US011937917B1

(12) United States Patent
Filatov et al.

(10) Patent No.: US 11,937,917 B1
(45) Date of Patent: Mar. 26, 2024

(54) DETECTING FALLS WITH MULTIPLE WEARABLE MOTION SENSORS

(71) Applicant: Alva Health Inc., New Haven, CT (US)

(72) Inventors: Denis Filatov, Mexico City (MX); Hitten Zaveri, New Haven, CT (US)

(73) Assignee: Alva Health Inc., New Haven, CT (US)

( * ) Notice: Subject to any disclaimer, the term of this patent is extended or adjusted under 35 U.S.C. 154(b) by 0 days.

(21) Appl. No.: 18/202,213

(22) Filed: Aug. 16, 2023

(51) Int. Cl.
*A61B 5/00* (2006.01)
*A61B 5/11* (2006.01)

(52) U.S. Cl.
CPC .......... *A61B 5/1117* (2013.01); *A61B 5/1118* (2013.01); *A61B 5/681* (2013.01)

(58) Field of Classification Search
None
See application file for complete search history.

(56) References Cited

U.S. PATENT DOCUMENTS

| 11,020,059 | B2 | 6/2021 | Sheth | |
|---|---|---|---|---|
| 11,282,361 | B2 | 3/2022 | Sharma | |
| 2015/0006446 | A1* | 1/2015 | Chiba | G01P 13/00 702/187 |
| 2019/0347922 | A1* | 11/2019 | Burton | A61B 5/1117 |
| 2020/0205746 | A1* | 7/2020 | Burwinkel | G16H 50/30 |
| 2021/0174663 | A1* | 6/2021 | Widgren | G08B 21/0446 |
| 2023/0000396 | A1* | 1/2023 | Coffey | A61B 5/1117 |
| 2023/0125403 | A1* | 4/2023 | Simmons | G06N 20/10 340/573.1 |

OTHER PUBLICATIONS

Adhikari et al., Activity Recognition for Indoor Fall Detection Using Convolutional Neural Network, 2017 Fifteenth IAPR International Conference on Machine Vision Applications (MVA), IEEE, May 8, 2017, pp. 81-84.
Bat-Erdene et al., Automatic Acute Stroke Symptom Detection and Emergency Medical Systems Alerting by Mobile Health Technologies: A Review, Journal of Stroke and Cerebrovascular Diseases, vol. 30, No. 7, Jul. 2021, pp. 1-9.
(Continued)

*Primary Examiner* — Benjamin S Melhus
(74) *Attorney, Agent, or Firm* — Van Pelt, Yi & James LLP

(57) ABSTRACT

In an example system, multi-sensor motion data that reflects the motion of a user over a period of time is received as recorded by a plurality of motion sensors on wearable devices, specific changes are determined in the data by, firstly, quantifying it using a two-dimensional data transform; secondly, extracting an anomalous area; and thirdly, calculating a number of the anomaly's properties, and the results are input into a machine learning model to detect that the user fell. The machine learning model processes the anomaly's properties and evaluates the current state of the user's activity by classifying the properties against a state space previously calculated by analyzing historical activities of daily living. Depending on a two-dimensional transform implemented, the machine learning model detects when the user falls, as well as potentially allows predicting that the user will suffer a fall in advance of the actual event, aiming at solving the stroke prediction problem.

20 Claims, 24 Drawing Sheets

(56) References Cited

OTHER PUBLICATIONS

Blanchard, Efficacy of a smartwatch application in detecting induced falls, Submitted to JMIR mHealth and uHealth, unpublished, non-peer-reviewed preprint, May 2, 2021, 20 pages, https://preprints.jmir.org/preprint/30121.

Botonis et al., Wearable airbag technology and machine learned models to mitigate falls after stroke, Journal of NeuroEngineering and Rehabilitation, 19(1):60, Jun. 17, 2022, pp. 1-14, https://doi.org/10.1186/s12984-022-01040-4.

Chelli et al., A Machine Learning Approach for Fall Detection and Daily Living Activity Recognition, IEEE Access, vol. 7, Mar. 21, 2019, pp. 38670-38687.

Filatov, On spatial synchronisation as a manifestation of irregular energy cascades in continuous media under the transition to criticality, Nonlinear Dynamics, 109(4), Jun. 16, 2022, pp. 2573-2594, https://doi.org/10.1007/s11071-022-07580-7.

Hakim et al., Smartphone Based Data Mining for Fall Detection: Analysis and Design, ScienceDirect, Procedia Computer Science 105, Jan. 1, 2017, pp. 46-51.

Harris, Mstroke: Methods of Fall Detection and Data Storage, A Thesis Submitted to the Faculty of the University of Tennessee at Chattanooga in Partial Fulfillment of the Requirements of the Degree of Master of Science: Computer Science, Dec. 2017, 45 pages.

Ihlen et al., The Discriminant Value of Phase-Dependent Local Dynamic Stability of Daily Life Walking in Older Adult Community-Dwelling Fallers and Nonfallers, BioMed Research International, Article ID 402596, Oct. 2015, 12 pages, http://dx.doi.org/10.1155/2015/402596.

Jahanjoo et al., Accurate Fall Detection Using 3-Axis Accelerometer Sensor and MLF Algorithm, 3rd International Conference on Pattern Recognition and Image Analysis (IPRIA 2017), Apr. 19-20, 2017, pp. 90-95.

Kao et al., GA-SVM applied to the fall detection system, Proceedings of the 2017 IEEE International Conference on Applied System Innovation (ICASI), May 13, 2017, pp. 436-439.

Kostopoulo et al., F2D: A location aware fall detection system tested with real data from daily life of elderly people, ScienceDirect, Procedia Computer Science 98, Jan. 1, 2016, pp. 212-219.

Liang et al., Fall Detection using Lifting Wavelet Transform and Support Vector Machine, Proceedings of the Federated Conference on Computer Science and Information Systems, ISSN 2300-5963 ACSIS, vol. 11, Sep. 3, 2017, pp. 877-883.

Liu et al., Impact of Sampling Rate on Wearable-based Fall Detection Systems Based on Machine Learning Models, IEEE Sensors Journal 18, No. 23, Sep. 30, 2018, pp. 9882-9890.

Lv et al., Information collection system for fall detection of stroke patients under cascade algorithm in the context of multi-modal information fusion and e-health, Expert Systems 40, No. 4, May 2023, pp. 1-11, https://doi.org/10.1111/exsy.12809.

Özdemir et al., Detecting Falls with Wearable Sensors Using Machine Learning Techniques, Sensors 2014, No. 14, ISSN 1424-8220, Jun. 18, 2014, pp. 10691-10708.

Putra et al., An Event-Triggered Machine Learning Approach for Accelerometer-Based Fall Detection, Sensors 2018, No. 1, Dec. 22, 2017, pp. 1-18.

Ralhan, A Study On Machine Learning Algorithms for Fall Detection and Movement Classification, PhD diss., Master's thesis, Department of Electrical and Computer Engineering, University of Saskatchewan, Dec. 2009, 67 pages.

Ramachandran et al., A Survey on Recent Advances in Wearable Fall Detection Systems, BioMed Research International, vol. 2020, Article ID 2167160, Jan. 13, 2020, pp. 1-17, https://doi.org/10.1155/2020/2167160.

Ramachandran et al., Machine Learning-based Fall Detection in Geriatric Healthcare Systems, 2018 IEEE International Conference on Advanced Networks and Telecommunications Systems (ANTS), Dec. 16, 2018, pp. 1-6.

Taylor-Piliae et al., Objective fall risk detection in stroke survivors using wearable sensor technology: a feasibility study, Topics in Stroke Rehabilitation, ISSN: 1074-9357 (Print) 1945-5119 (Online), May 10, 2016, 8 pages, http://dx.doi.org/10.1179/1074935715Z.00000000059.

Tran et al., A multi-modal multi-view dataset for human fall analysis and preliminary investigation on modality, 2018 24th International Conference on Pattern Recognition (ICPR), Aug. 20-24, 2018, pp. 1947-1952.

Wang et al., An Improved Fall Detection Approach for Elderly People Based on Feature Weight and Bayesian Classification, Proceedings of 2016 IEEE International Conference on Mechatronics and Automation, Aug. 7-10, 2016, pp. 471-476.

Weiss et al., Does the Evaluation of Gait Quality During Daily Life Provide Insight Into Fall Risk? A Novel Approach Using 3-Day Accelerometer Recordings, Neurorehabilitation and Neural Repair 27, No. 8, Oct. 2013, pp. 742-752.

Yang et al., A Wearable Real-Time Fall Detector Based On Naive Bayes Classifier, In CCECE 2010 IEEE, May 2, 2010, pp. 1-4.

Yu et al., Hidden Markov Model-Based Fall Detection with Motion Sensor Orientation Calibration: A Case for Real-Life Home Monitoring, IEEE Journal of Biomedical and Health Informatics 22, No. 6, Dec. 11, 2017, pp. 1847-1853.

\* cited by examiner

US 11,937,917 B1

DETECTING FALLS WITH MULTIPLE WEARABLE MOTION SENSORS

BACKGROUND OF THE INVENTION

A motion sensor is part of a wearable device that measures the motion experienced by a user while the device is worn on the body. The measurements recorded by the motion sensor over a period of time can be used to determine different types of activities, including falls (if any) during that period, by quantifying the specific changes in the data typical for each of the user's activities.

BRIEF DESCRIPTION OF THE DRAWINGS

Various embodiments of the invention are disclosed in the following detailed description and the accompanying drawings.

DETAILED DESCRIPTION

Figure 1:
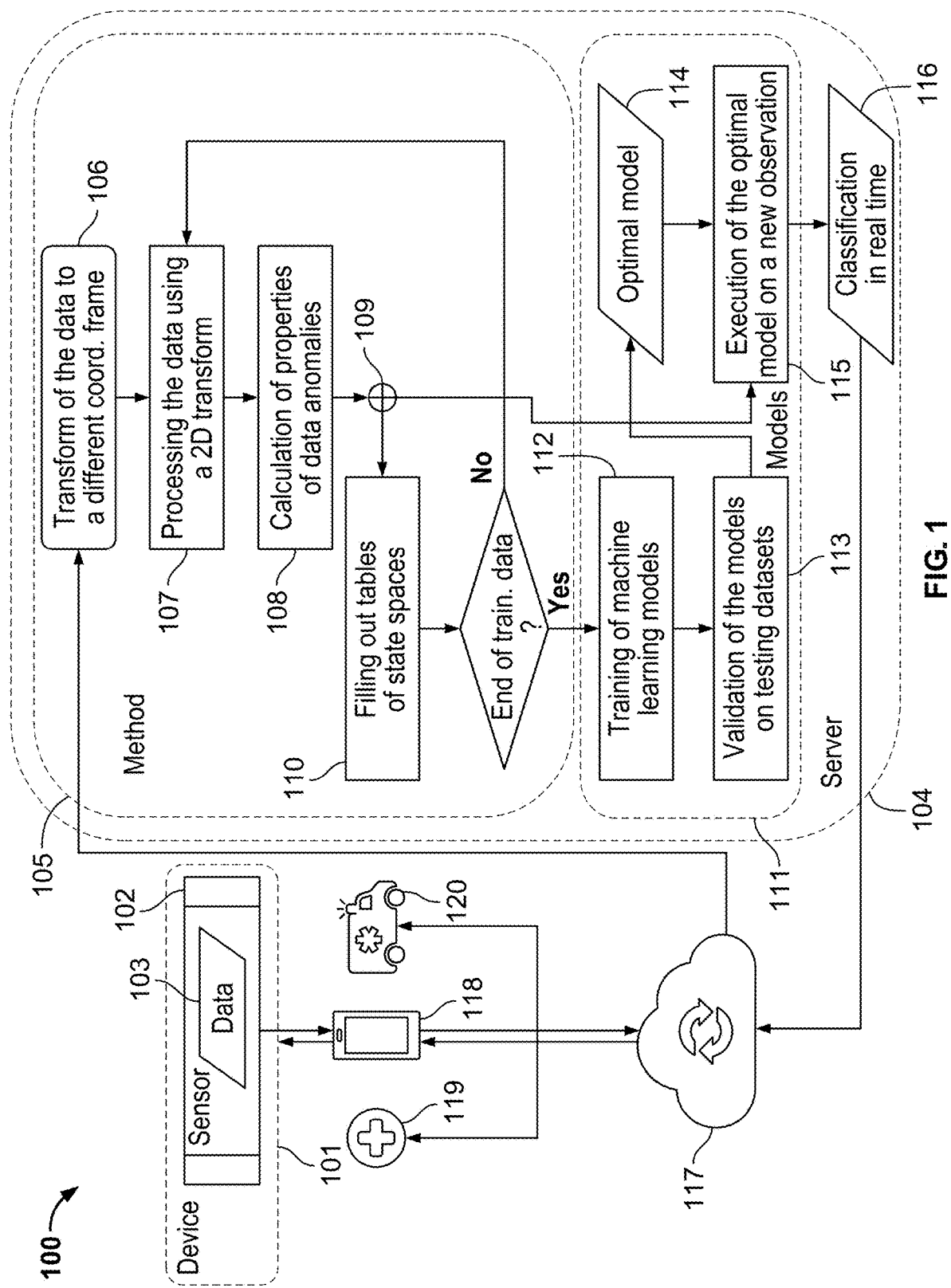
FIG. 1 shows a fall detection system that comprises a single wearable device producing a 3D single-sensor time series of the user's motion, a computational method based on a two-dimensional data transform, and machine learning models either to be trained on the method's outputs using a training dataset and then validated on a testing dataset for producing an optimal model or to be used for real-time classification of the user's activities.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Falls are known to be a major hallmark of stroke, and therefore, an AI-based system that can detect and predict falls is an essential part of a neuromonitoring platform for real-time detection of strokes.

The existing AI-based systems primarily focus on fall detection that is intended to recognize an event after it has already happened.

There is room for building an AI-based system to continuously analyze the user's behavior and not only detect but also predict falls by duly quantifying changes in the user's physiological parameters and thus recognizing an upcoming fall in advance.

Thus, what is needed are new and improved techniques for detecting falls and for predicting falls.

Overview of Techniques for Detecting Falls Using Multiple Wearable Motion Sensors In an aspect the detection of falls is performed by a system that includes (1) a wearable device worn by the user, (2) a motion sensor installed in the device, (3) data reflecting the user's motion and measured by the sensor (e.g., a motion sensor) over a period of time, (4) a computational method that determines the specific changes in the data typical for each of the user's daily activities, and (5) a machine learning model that firstly, using the previously quantified changes, gets trained on the user's different activities and then, for every new observation, determines if the user has fallen or has performed a daily, non-fall-related activity.

Implementations of this aspect include the following features.

In some implementations the data recorded by the motion sensor is a three-component vector measuring the acceleration in the three sensor-related spatial directions.

In some implementations the data recorded by the motion sensor can be a one- or a two-component acceleration vector.

The data recorded by the motion sensor is sampled at a rate not less than 20 Hz.

For a fixed component of the acceleration vector the computational method encompasses the calculation of a two-dimensional transform of a portion of the data of length L=15 seconds and the subsequent determination of the areas (the so-called "T-anomalies") where the transform's absolute square is above a threshold.

In some implementations the length L of the portion of the data processed by the computational method can be less or greater than 15 seconds.

In some implementations the calculation of the data's two-dimensional transform can be based on a continuous wavelet transform.

Under the same portion of the data, for the found T-anomalies, the computational method further comprises the calculation of n=8 properties, or features: the maximum magnitude, the time range, the frequency range, the area, the total energy, the center in time, the center in frequency, and the fractal dimension; when taken in all possible k-dimensional combinations among the given number of n properties, $1 \leq k \leq n$, forms n tables of state spaces of sizes $$\frac{n!}{(n-k)!k!}$$

rows (number of all possible state spaces of dimensionality k) by k columns (number of properties defining axes of the corresponding state space).

In some implementations the acceleration data processed by the computational method can be the data measured in the original coordinate frame of the motion sensor.

In some implementations the acceleration data processed by the computational method can be the data transformed from the original sensor-related coordinate frame to a horizontal coordinate frame parallel to the Earth's surface, or perpendicular to the gravity vector (the so-called "H-transformed data").

In some implementations the acceleration data processed by the computational method can be the data transformed from the original sensor-related coordinate frame to a vertical coordinate frame perpendicular to the Earth's surface, or collinear to the gravity vector (the so-called "V-transformed data").

Using the same fixed component of the acceleration vector, the computational method processes the data in a moving window of length L seconds, producing a sequence of the properties of T-anomalies of length N observations and thereby filling each of the rows of the n tables of state spaces with N entries; thus, for a parameter k, each of the $$\frac{n!}{(n-k)!k!}$$

rows of the kth table of state spaces contains a table of observations for the user's activities of size N rows (number of observations) by k columns (number of properties).

All tables of observations are divided into two datasets each: a training dataset and a testing dataset.

Using the first datasets, for a fixed parameter k, machine learning models (called "T-models") get trained by classifying the user's activities within each of the $$\frac{n!}{(n-k)!k!}$$

state spaces into two clusters, one related to falls and the other related to non-falls, or activities of daily living.

In some implementations the classification clusters can be generated using a support vector machine classifier.

The assignment of one of the two clusters to falls is based on the empirical evidence that within certain ranges of values the above-given eight properties of T-anomalies of the data's two-dimensional transform are specific for activities associated with falls.

In some implementations the observed T-anomalies in the data's two-dimensional transform can be classified into a larger number of clusters, allowing a separation of the user's non-fall-related activities into different types.

Using the second data sets, the machine learning models get validated by providing classifications for the test observations and by computing fall-related false positive rates, fall-related false negative rates, and fall-related total false rates.

For practical purposes, for a fixed parameter k, a comparison of the fall-related total false rates over all possible $$\frac{n!}{(n-k)!k!}$$

state spaces yields the local, k-dimensional optimal state space, while a subsequent comparison over all the n dimensionalities yields the general optimal state space.

The general optimal state space determines the optimal transform-based machine learning model (called the "optimal T-model") allowing the most accurate detection of falls and their separation from daily, non-fall-related activities.

In some implementations the above-described computational method and the machine learning models can be applied to several or all components of the acceleration vector.

In another aspect the detection of falls is performed by a system that comprises (1) multiple wearable devices, each with a motion sensor installed therein, worn on different parts of the user's body, (2) multi-sensor data reflecting motion of the corresponding parts of the user's body, (3) a computational method that determines the specific changes in the multi-sensor data typical for each of the user's daily activities, and (4) a machine learning model that firstly, using the previously quantified changes in the multi-sensor data, gets trained on the user's different activities and then, for every new observation, determines if the user has fallen or has performed a non-fall-related activity.

Implementations of this aspect include the following features.

In some implementations the system can have two wearable motion sensors, each worn on one of the two of the user's wrists, thus producing two-sensor data.

In some implementations the data recorded by each of the multiple motion sensors is a three-component vector measuring the acceleration in the three sensor-related spatial directions.

In some implementations the data recorded by each of the multiple motion sensors can be a one- or a two-component acceleration vector.

The data recorded by each of the multiple motion sensors is sampled at the rate not less than 20 Hz.

For a fixed component of the multi-sensor acceleration vector, for each of the one-sensor time series, the computational method encompasses the calculation of a two-dimensional transform of a portion of the data of length L seconds and the subsequent averaging of the result in frequency. This procedure works as a smoothing filter eliminating noises from the data and leaving only trends in them.

In some implementations the smoothing filter can be based on a continuous wavelet transform as the data's two-dimensional transform.

For every of the smoothed portions of the data the first derivatives in time are calculated to ensure stationarity.

For the smoothed stationary portions of the multi-sensor data the computational method further encompasses the calculation of a total coherence field between them and the subsequent determination of the areas (the so-called "C-anomalies") where the total coherence is above a threshold.

In some implementations the calculation of the total coherence field can be based on using wavelets as the basis function of the underlying spectral coherence analysis.

For the same portion of the multi-sensor data, for the found C-anomalies, the computational method further comprises the calculation of n=8 properties: the maximum magnitude, the time range, the frequency range, the area, the total energy, the center in time, the center in frequency, and the fractal dimension; when taken in all possible k-dimensional combinations among the given number of n properties, 1≤k≤n, forms n tables of state spaces of sizes $$\frac{n!}{(n-k)!k!}$$

rows (number of all possible state spaces of dimensionality k) by k columns (number of properties defining axes of the corresponding state space).

In some implementations the multi-sensor acceleration data processed by the computational method can be the data measured in the original coordinate frames of the motion sensors.

In some implementations the multi-sensor acceleration data processed by the computational method can be the data (the so-called "H-transformed data") transformed from the original sensor-related coordinate frames to a horizontal coordinate frame parallel to the Earth's surface, or perpendicular to the gravity vector.

In some implementations the multi-sensor acceleration data processed by the computational method can be the data (the so-called "V-transformed data") transformed from the original sensor-related coordinate frames to a vertical coordinate frame perpendicular to the Earth's surface, or collinear to the gravity vector.

Using the same fixed component of the multi-sensor acceleration vector, the computational method processes the multi-sensor data in a moving window of length L seconds, producing a sequence of the properties of C-anomalies of length N observations and thereby filling each of the rows of the n tables of state spaces with N entries; thus, for a fixed parameter k each of the $$\frac{n!}{(n-k)!k!}$$

rows of the kth table of state spaces contains a table of observations for the user's activities of size N rows (number of observations) by k columns (number of properties).

All tables of observations are divided into two datasets each: a training dataset and a testing dataset.

Using the first datasets, for a fixed parameter k, machine learning models (called "C-models") get trained by classifying the user's activities within each of the $$\frac{n!}{(n-k)!k!}$$

state spaces into two clusters, one related to falls and the other related to non-falls, or activities of daily living.

In some implementations the clusters can be generated using a support vector machine classifier.

The assignment of one of the two clusters to falls is based on the empirical evidence that within certain ranges of values the above-given eight properties of C-anomalies of the multi-sensor data's total coherence field are specific for activities associated with falls.

In some implementations the observed C-anomalies in the total coherence field can be classified into a larger number of clusters, allowing to separate the user's non-fall-related activities into different types.

Using the second data sets, the machine learning models get validated by providing classifications for the test observations and by computing fall-related false positive rates, fall-related false negative rates, and fall-related total false rates.

For practical purposes, for a fixed parameter k, a comparison of the fall-related total false rates over all possible $$\frac{n!}{(n-k)!k!}$$

stat spaces yields the local, k-dimensional optimal state space, while a subsequent comparison over all the n dimensionalities yields the general optimal state space.

The general optimal state space determines the optimal coherence-based machine learning model (called the "optimal C-model") allowing the most accurate detection of falls and their separation from non-fall-related activities.

An advantage of a coherence-based fall detection system is that it may allow to quantify the specific long-term changes that occur in the motion of a user exposed to a higher risk of stroke on a scale of days or weeks. Such changes are associated with a higher degree of synchronization of the motion of different parts of the body. The quantification of long-term synchronization-associated motion changes may allow solving not only the problem of fall detection, that is the detection of an event that has already happened, but also solving the problem of fall prediction—probabilistic forecasting an event that will likely occur in the near future.

In some implementations the above-described computational method and the machine learning models can be applied to several or all components of the multi-sensor acceleration vector.

In another aspect the detection of falls is performed by a system that comprises (1) multiple wearable devices, each with a motion sensor installed therein, worn on different parts of the user's body, (2) multi-sensor data reflecting motion of the corresponding parts of the user's body, (3) a one-sensor and a multi-sensor computational methods that, each in its own manner, determine the specific changes in certain subsets of the data typical for every of the user's daily activities, (4) several machine learning models that firstly, using the previously quantified changes in the corresponding data subsets, get trained on the user's different activities and then, for every new observation, independently vote for if the user has fallen or has performed a non-fall-related activity, and (5) a computational method (called the "elector") that takes into account the votes made by each of the models and, based on the votes, makes a final decision about the user's current activity.

Implementations of this aspect include the following features.

In some implementations the system can have two wearable motion sensors, each worn on one of the user's wrists, thus producing two-sensor data.

In some implementations the data recorded by each of the multiple motion sensors is a three-component vector measuring the acceleration in the three sensor-related spatial directions.

In some implementations the data recorded by each of the multiple motion sensors can be a one- or a two-component acceleration vector.

The data recorded by each of the multiple motion sensors is sampled at a rate of not less than 20 Hz.

For a fixed component of the multi-sensor acceleration vector, for each of the one-sensor time series, the one-sensor computational method encompasses the calculation of a two-dimensional transform of a portion of the data of length L seconds.

In some implementations the calculation of the data's two-dimensional transform can be based on a continuous wavelet transform.

For each of the obtained two-dimensional transforms (i) the areas (called "T-anomalies") where the transform's absolute square is above a threshold are determined, and (ii) the mean obtained by averaging the transform in frequency, aimed at smoothing the data by eliminating noises and leaving only trends in them, is calculated.

For every of the smoothed portions of the data the first derivatives in time are calculated to ensure stationarity.

For the smoothed stationary portions of the multi-sensor data the multi-sensor computational method encompasses the calculation of a total coherence field between them and the subsequent determination of the areas (called "C-anomalies") where the total coherence is above a threshold.

In some implementations the calculation of the total coherence field can be based on using wavelets as the basis function of the underlying spectral coherence analysis.

For the same portion of the multi-sensor data, for the found T-anomalies of each of the one-sensor time series, the one-sensor computational method further comprises the calculation of n=8 properties: the maximum magnitude, the time range, the frequency range, the area, the total energy, the center in time, the center in frequency, and the fractal dimension; when taken in all possible k-dimensional combinations among the given number of n properties, $1 \leq k \leq n$, forms the corresponding n tables of state spaces (called "T-tables") of sizes $$\frac{n!}{(n-k)!k!}$$

rows by k columns.

For the same portion of the multi-sensor data, for the found C-anomalies, the multi-sensor computational method further comprises the calculation of n=8 properties: the maximum magnitude, the time range, the frequency range, the area, the total energy, the center in time, the center in frequency, and the fractal dimension; when taken in all possible k-dimensional combinations among the given number of n properties, $1 \leq k \leq n$, forms n tables of state spaces (called "C-tables") of sizes $$\frac{n!}{(n-k)!k!}$$

rows by k columns.

In some implementations the multi-sensor acceleration data processed by both computational methods can be the data measured in the original coordinate frame of the motion sensors.

In some implementations the multi-sensor acceleration data processed by both computational methods can be the data (the so-called "H-transformed data") transformed from the original sensor-related coordinate frames to a horizontal coordinate frame parallel to the Earth's surface, or perpendicular to the gravity vector.

In some implementations the multi-sensor acceleration data processed by both computational methods can be the data (the so-called "V-transformed data") transformed from the original sensor-related coordinate frames to a vertical coordinate frame perpendicular to the Earth's surface, or collinear to the gravity vector.

For the same fixed component of the multi-sensor acceleration vector, for every of the one-sensor time series the one-sensor computational method processes the data in a moving window of length L seconds, producing a sequence of the properties of T-anomalies of length N observations and thereby filling each of the rows of the corresponding n T-tables of state spaces with N entries; thus, for a fixed parameter k each of the $$\frac{n!}{(n-k)!k!}$$

rows of the corresponding kth T-table of state spaces contains a table of observations for the user's activities of size N rows by k columns.

Using the same fixed component of the multi-sensor acceleration vector, the multi-sensor computational method processes the multi-sensor data in a moving window of length L seconds, producing a sequence of the properties of C-anomalies of length N observations and thereby filling each of the rows of the n C-tables of state spaces with N entries; thus, for a fixed parameter k each of the $$\frac{n!}{(n-k)!k!}$$

rows of the kth C-table of state spaces contains a table of observations for the user's activities of size N rows by k columns.

All tables of observations, coming both from the T- and C-tables of state spaces, are divided into two datasets each: a training dataset and a testing dataset.

Using the first datasets, for every fixed set of T- or C-tables of state spaces, for a fixed parameter k, machine learning T- or C-models get trained by classifying the user's activities within each of the $$\frac{n!}{(n-k)!k!}$$

state spaces into two clusters, one related to falls and the other related to non-falls, or activities of daily living.

In some implementations the clusters can be generated using a support vector machine classifier.

In some implementations the observed anomalies can be classified into a larger number of clusters, allowing to separate the user's non-fall-related activities into different types.

Using the second data sets, the machine learning models get validated by providing classifications for the test observations.

The computational method (the "elector") summarizes the classifications, or votes, made by all the T- and C-models and makes a final decision providing the ultimate classification for every test observation, thus defining voting-based models (the "V-models").

For the resulting voting-based models fall-related false positive rates, fall-related false negative rates and fall-related total false rates are computed.

For practical purposes, for a fixed parameter k a comparison of the fall-related total false rates over all possible $$\frac{n!}{(n-k)!k!}$$

state spaces yields the local, k-dimensional optimal state space, while a subsequent comparison over all the n dimensionalities yields the general optimal state space.

The general optimal state space determines the optimal voting-based machine learning model (called the "optimal V-model") allowing the most accurate detection of falls and their separation from daily, non-fall-related activities.

An advantage of the voting-based models that use the outputs of several independent T- and C-models is that they may allow to increase the classification accuracy by minimizing the total false rates compared to using each of the T- or C-models alone.

In some implementations the above-described computational methods and the machine learning models can be applied to several or all components of the multi-sensor acceleration vector.

Embodiments for Detecting Falls Using Multiple Wearable Motion Sensors

Single-Device Transform-Based System

The general structure of a system 100 for determining if a user has fallen is shown in FIG. 1.

The system 100 includes (1) a wearable device 101 with a motion sensor 102, (2) data 103 recorded by the sensor, (3) a computational method 105 and (4) machine learning models 111.

The computational method 105 may optionally contain a block 106 that preliminarily transforms the data 103 from the original sensor-related coordinate frame to a special coordinate frame.

The computational method 105 and the machine learning models 111 operate in two different modes, depending on the state of a switch 109.

In the training mode the data 103 is a finite dataset obtained either on a person-specific basis, using historical data that had been collected from activities of a given user, or on a universal basis, using historical data that had been collected from activities of a cohort of users.

In the training mode the computational method 105 comprises (i) a block 107 for processing the data using a two-dimensional transform, (ii) a block 108 for extraction of anomalies present in the two-dimensional transform and subsequent calculation of properties, or features, of the extracted anomalies, and (iii) a block 110 for preparing observation tables that comprise arrays of values in all possible combinations of the calculated properties, so that each observation table contains an array of values in a given combination of the properties.

In the training mode the machine learning models 111 comprise (i) a block 112 for teaching the models on training datasets and (ii) a block 113 for model validation that, using testing datasets, determines an optimal model 114 to be used in the execution mode.

In the training mode the optimal model 114 is trained before the first use of the system 100.

In the training mode the optimal model 114 may sometimes get retrained on a newly obtained finite dataset.

In the execution mode the data 103 is a continuous stream for the duration of monitoring being obtained on a person-specific basis.

In the execution mode the computational method 105 mandatorily comprises (i) the block 107 for processing the data using a two-dimensional transform and (ii) the block 108 for extraction of anomalies and subsequent calculation of their properties.

In the execution mode the machine learning models 111 comprise (i) the block 114 of the previously determined optimal model and (ii) a block 115 where the optimal model is applied to the properties calculated by the block 108 for taking a decision 116 whether it was a fall or another activity of daily living.

In some implementations the system 100 is a client-server solution, where the wearable device 101 with the motion sensor 102 is deployed on the client side, while the computational method 105 and the machine learning models 111 are run on the server side using an external computer 104 (e.g., a server).

In a client-server implementation of the system 100 the data 103 is transmitted from the client to the server by a communication means 118 (e.g., a smartphone) via a network 117 (e.g., wi-fi, a cellular network, etc.). In the same manner, the result of classification 116 is transmitted back from the server 104 to the client 101.

In some implementations in case if the user has fallen, the classification result 116 may additionally be transmitted to receivers that comprise one or more separate entities, e.g., the individual's caretaker 119, an emergency system 120, etc.

A client-server architecture may be needed for various reasons, e.g., if the computational method 105 and/or the machine learning models 111 cannot be run on the wearable device 101 because of its limited computational capacity, limited battery life, etc.

In some implementations, e.g., if the computational capacity allows it, the server side of the system 100 can be deployed in the smartphone.

Figure 2:
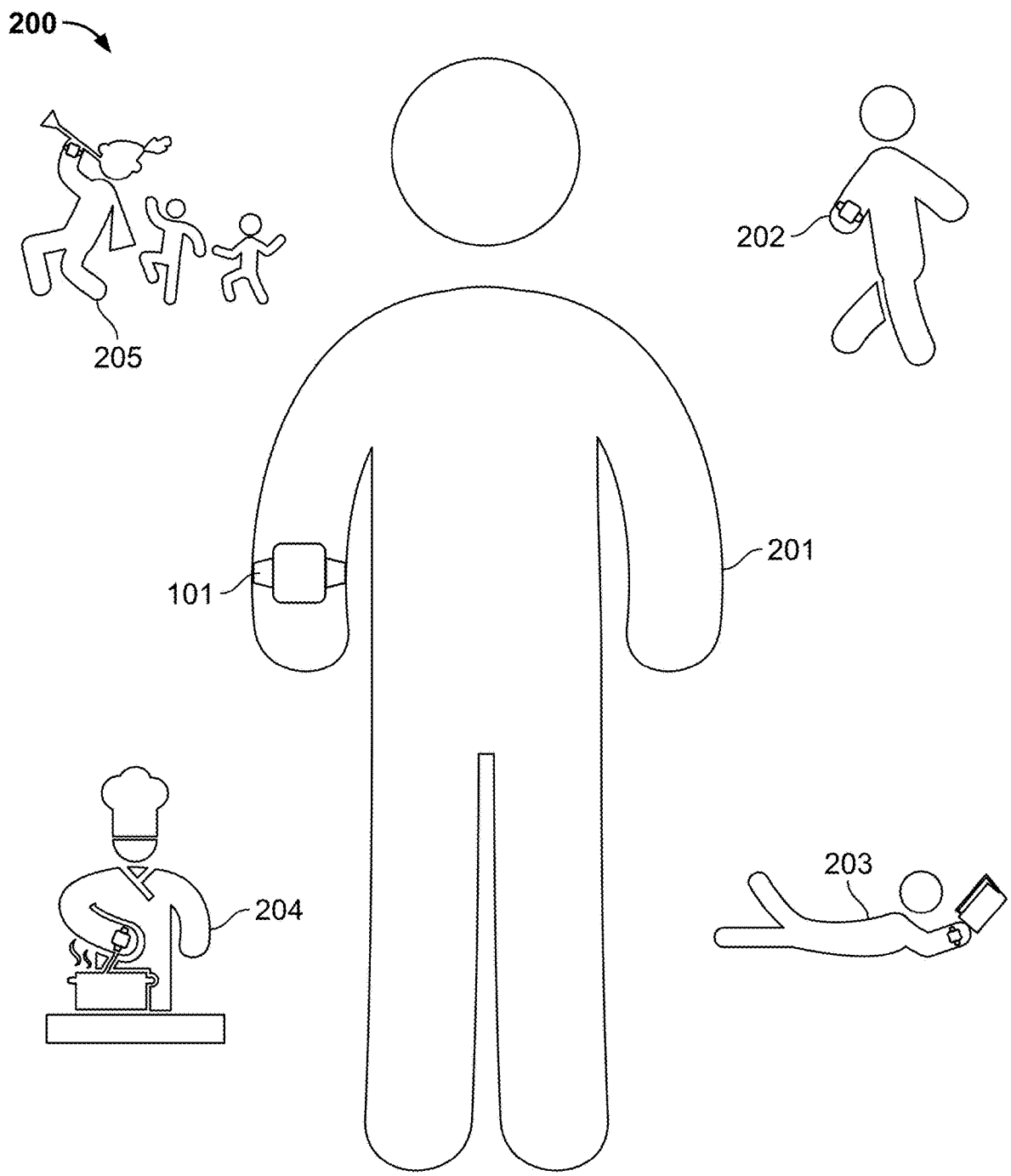
FIG. 2 shows a placement of a wearable device on a human body and illustrates examples of activities of daily living.

An example of functioning of the system 100 is shown in FIG. 2, where different types of the user's activities 200 are shown. The user 201 places the wearable device 101 on a wrist and goes about daily life, e.g., walking 202, lying 203, cooking 204, playing 205 etc., while the device's sensor 102 collects the data 103 as an acceleration vector in space. The user's movements can include walking, running, jumping, staying in quiescence, making phone calls, or committing any other physical activity as part of daily life. All the collected information is further used by the computational method 105 and the machine learning models 111 to classify the user's activity and to detect if there have been falls.

In practice the wearable device 101 can be placed on other parts of the user's body, not necessarily a wrist,—e.g., on an arm, ankle, or hip.

Figure 3:
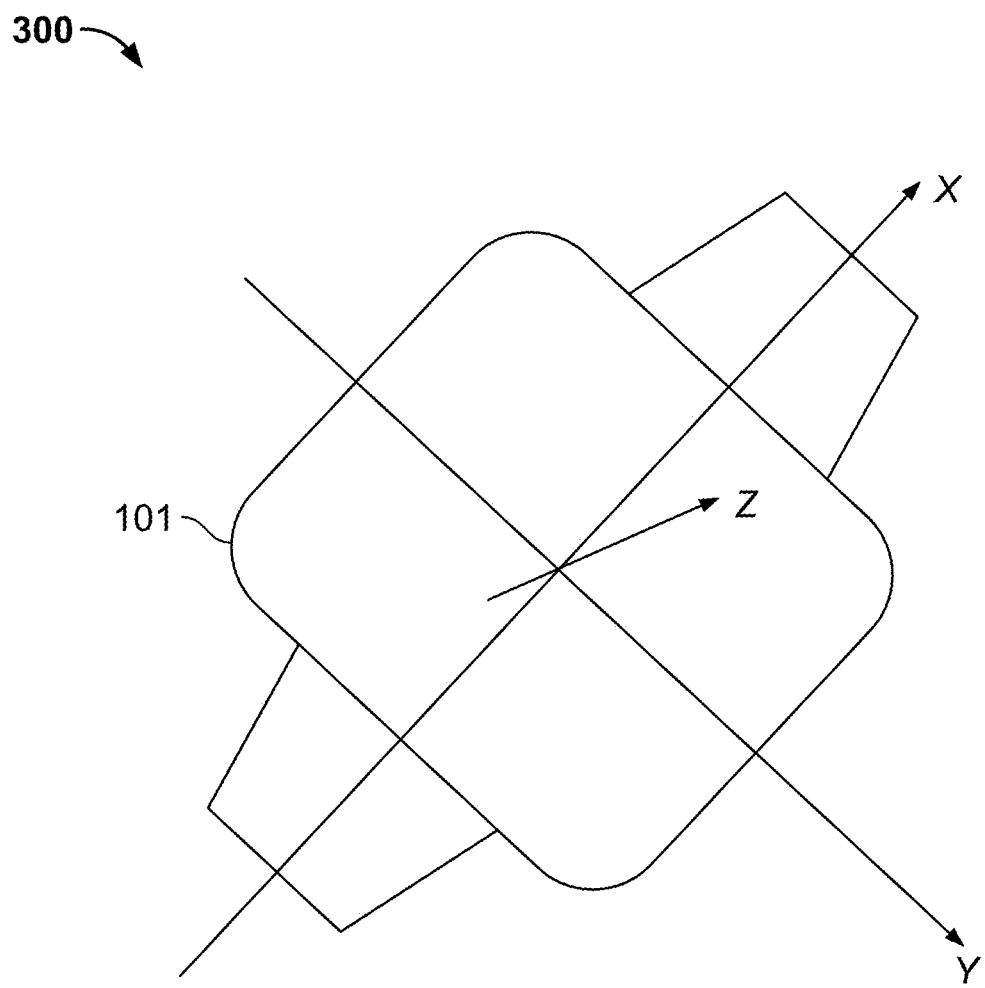
FIG. 3 shows a wearable device and the orientation of three spatial axes, X (anterior-posterior), Y (medio-lateral) and Z (vertical) determining the sensor-related coordinate frame XYZ, with respect to it.

The wearable device 101 with an example of a sensor-related coordinate frame XYZ is shown in FIG. 3 as a general schema 300. While the device's sensor 102 is collecting the data 103, they are recorded with respect to the sensor's coordinate frame which, unless the user does not move, is continuously changing its orientation in space.

For each component of the acceleration vector the data 103 is being recorded at a sampling rate not less than 20 Hz.

Although in FIG. 3 the sensor-related coordinate frame is illustrated to contain three axes, which implies recording a three-dimensional acceleration vector, in practice, depending on the technical implementations of the sensor 102, the coordinate frame can contain from one to three spatial axes, thus determining the corresponding number of components in the acceleration vector.

In some implementations the sensor 102 can also measure orientation in space, thus recording from one to three angular velocities.

In some implementations the sensor 102 can also measure magnetic field around the device, thus recording, depending on the technical characteristics, the direction, strength, or relative change of the field.

In some implementations the collected data 103 is passed to the processing 107 as is, without the preliminary transform 106.

In some implementations the collected data 103, before being passed to the processing 107, is preliminarily transformed from the original, sensor-related coordinate frame XYZ to a specific coordinate frame X' Y'Z'.

Figure 4:
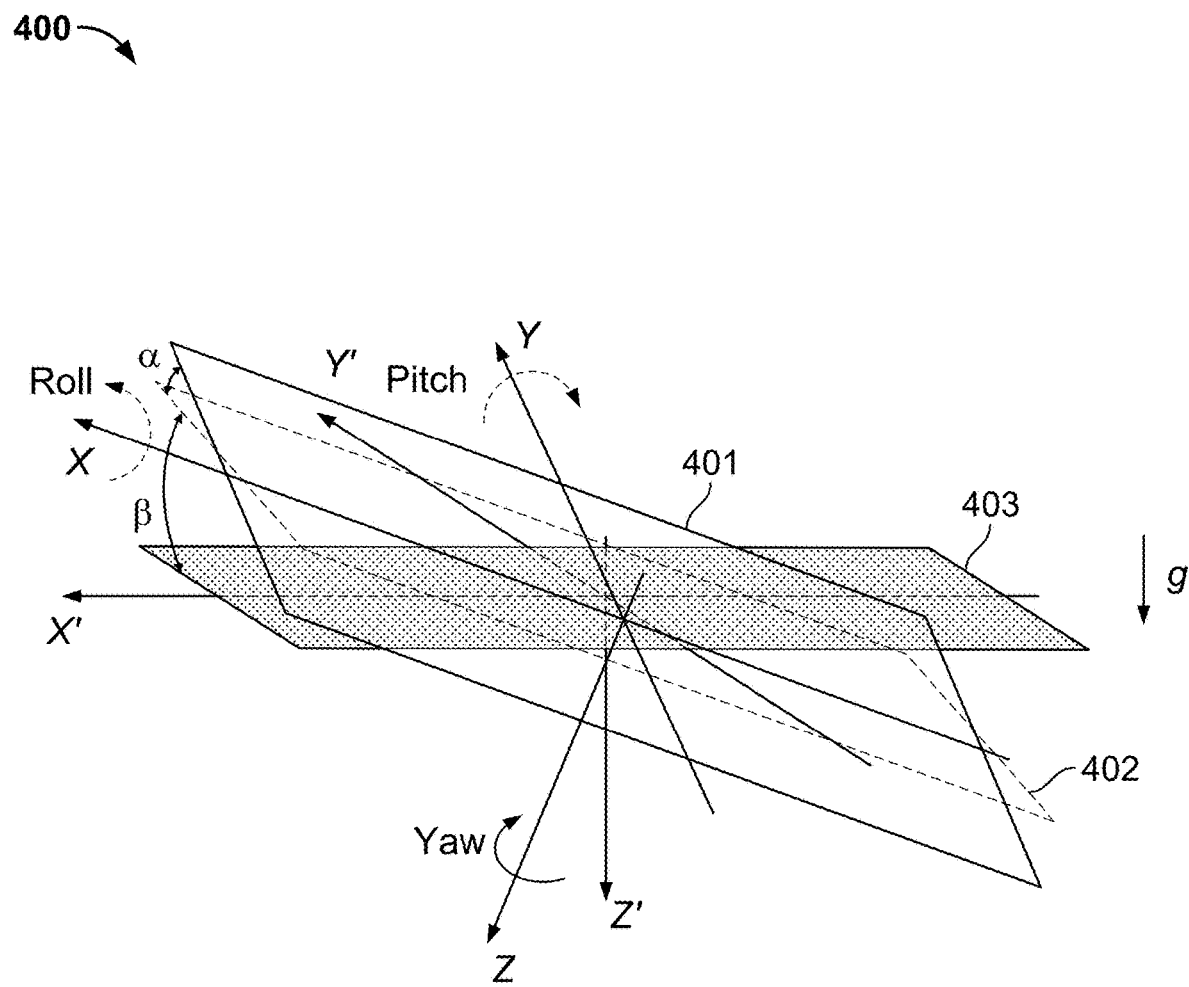
FIG. 4 shows a transform of the original sensor-related coordinate frame XYZ to a horizontal coordinate frame X'Y'Z' parallel to the Earth's surface, or perpendicular to the gravity vector g.

As an example, FIG. 4, in a general 3D view 400, shows a transform of the sensor-related coordinate frame XYZ to a coordinate frame X' Y'Z' whose first two axes X' and Y' form a horizontal plane 403 perpendicular to the gravity vector g. In doing so, the plane 401 formed by the axes X and Y of the original coordinate frame is first rotated around the X-axis by the roll angle $$\alpha = \tan^{-1}\left(\frac{X}{\sqrt{Y^2 + Z^2}}\right),$$

thus, yielding the intermediate plane 402, and is further rotated around the Y-axis by the pitch angle $$\beta = \tan^{-1}\left(\frac{Y}{\sqrt{X^2 + Z^2}}\right),$$

yielding the final plane 403. The components $q_i(t)$'s of the original, sensor-related d-dimensional acceleration vector $q=(q_1, \ldots, q_d)$ are transformed as follows $$R_X = \begin{pmatrix} 1 & 0 & 0 \\ 0 & \cos\alpha & -\sin\alpha \\ 0 & \sin\alpha & \cos\alpha \end{pmatrix}, R_Y = \begin{pmatrix} \cos\beta & 0 & \sin\beta \\ 0 & 1 & 0 \\ -\sin\beta & 0 & \cos\beta \end{pmatrix}, q'_i(t) = R_Y^{-1} R_X^{-1} q_i(t),$$

yielding the H-transformed data $q'=(q_1', \ldots q_d')$.

Figure 5:
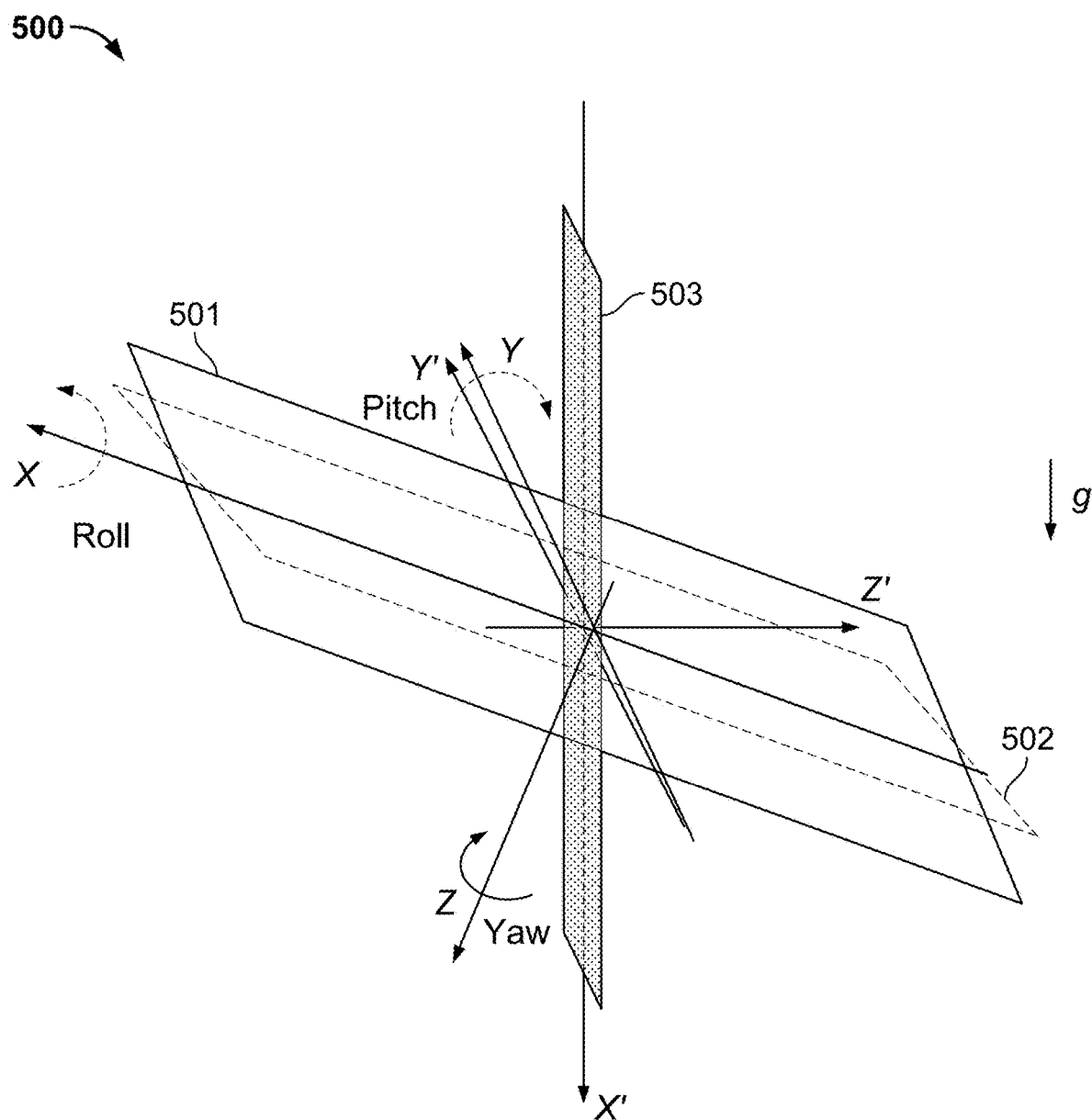
FIG. 5 shows a transform of the original sensor-related coordinate frame XYZ to a vertical coordinate frame X'Y'Z' perpendicular to the Earth's surface, or collinear to the gravity vector g.

As another example, FIG. 5, in a general 3D view 500, shows a transform of the sensor-related coordinate frame XYZ to a coordinate frame X'Y'Z' whose first two axes X' and Y' form a vertical plane 503 collinear to the gravity vector g. In doing so, the plane 501 formed by the axes X and Y of the original coordinate frame is first rotated around the X-axis by the roll angle α as above, thus yielding the intermediate plane 502, and is further rotated around the Y-axis by the pitch angle $$\beta = \tan^{-1}\left(\frac{Y}{\sqrt{X^2 + Z^2}}\right) + \frac{\pi}{2},$$

yielding the final plane 503. The components of the original, sensor-related acceleration vector are transformed by the same formulas as above, yielding the V-transformed data.

Figure 6:
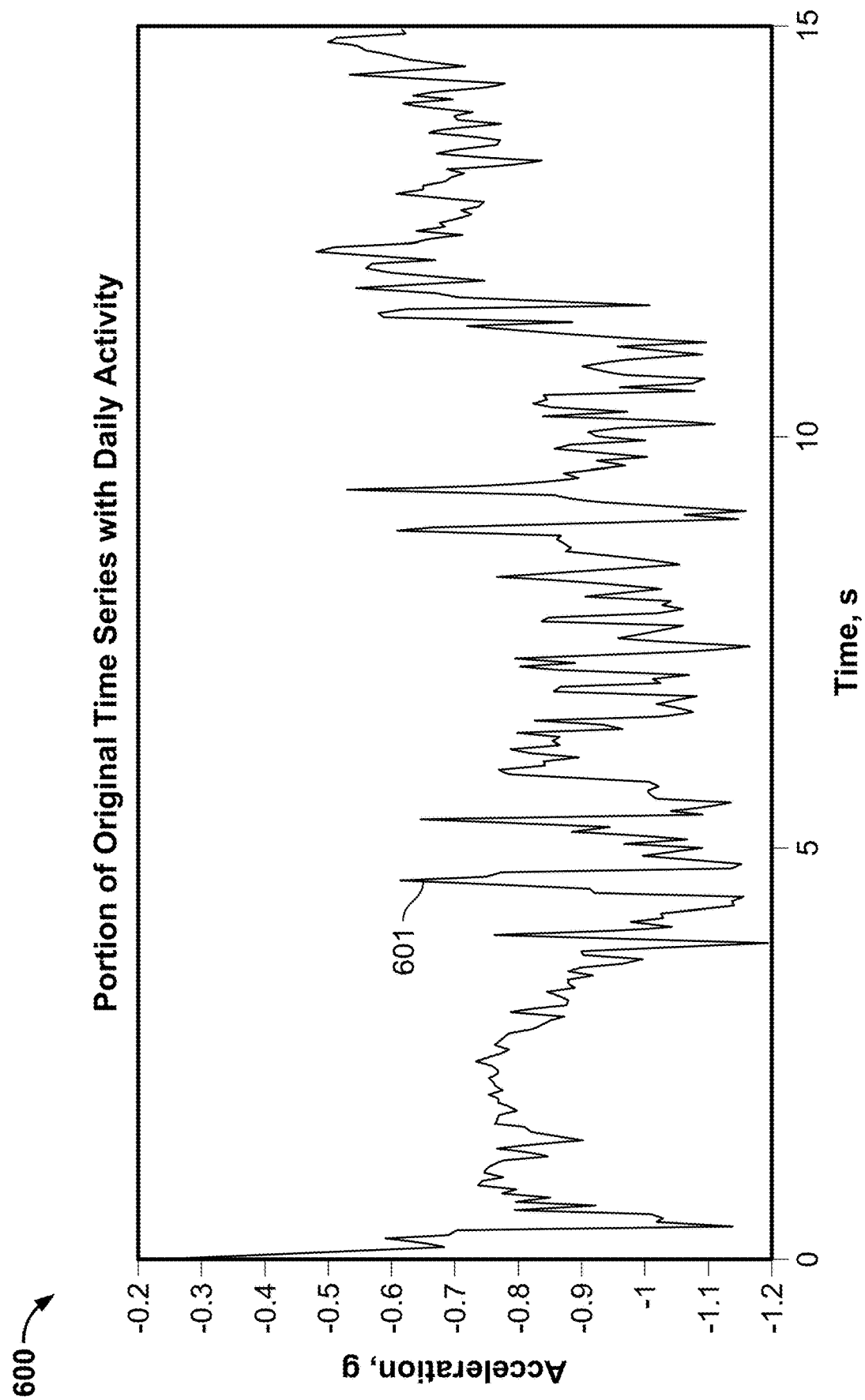
FIG. 6 shows a 15-seconds-long portion of one spatial component of a 3D time series of accelerations recorded by a wearable device when the user performs activities of daily living, i.e., in the absence of falls.

FIG. 6, on a 2D plot 600, shows an example of a 15-seconds-long portion of the data 103 containing a period of daily, non-fall-related, activity. The data represents temporal variations 601 of a component of the acceleration vector in the sensor-related coordinate frame. As seen in FIG. 6, daily activities normally evince a behavior with small amplitudes and low complexity, without clear trends or specific changes present in the data.

Figure 7:
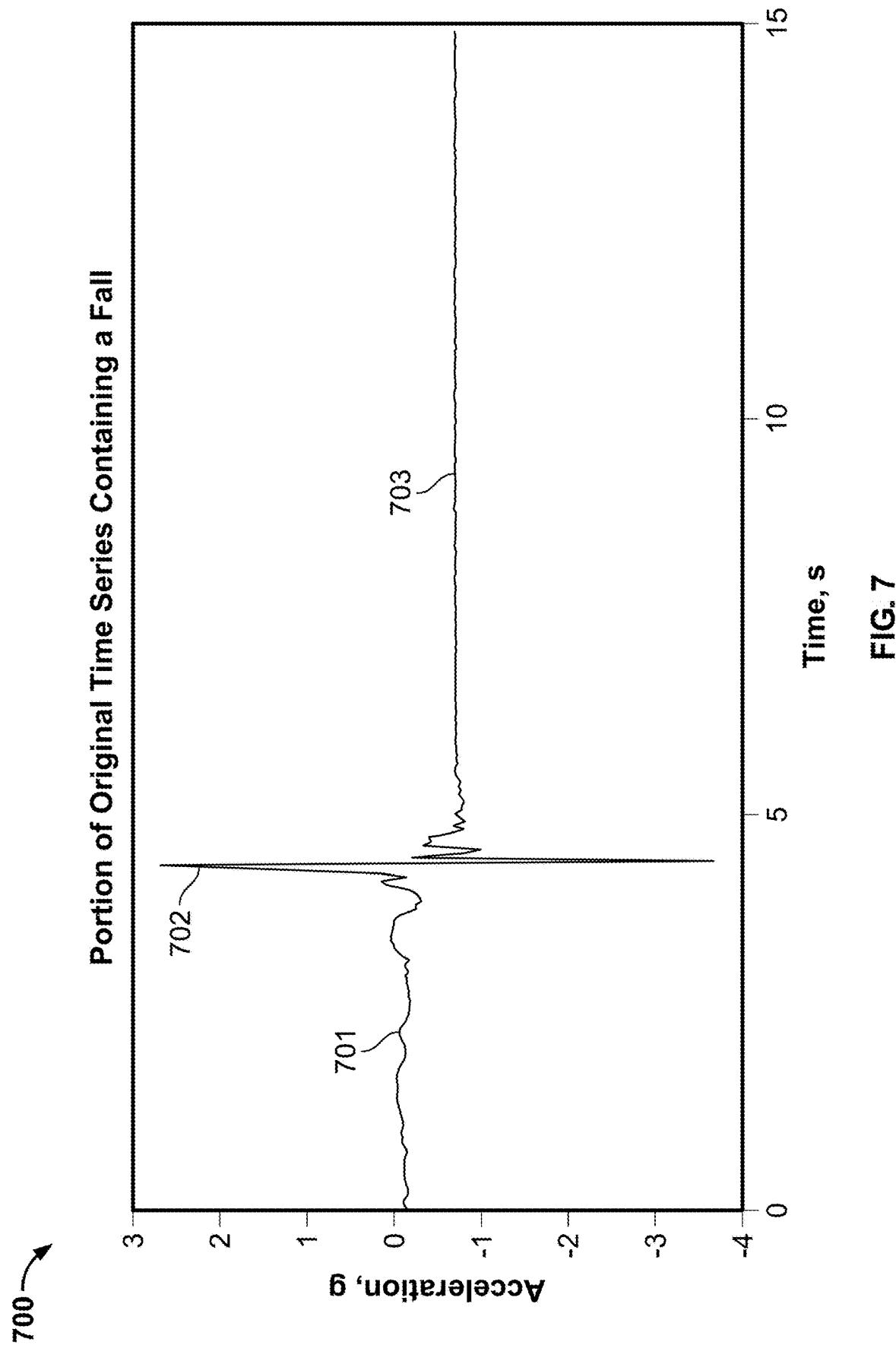
FIG. 7 shows a 15-seconds-long portion of one spatial component of a 3D time series of accelerations recorded by a wearable device when the user experiences a fall.

FIG. 7, on a 2D plot 700, shows an example of a 15-seconds-long portion of the data 103 containing a fall. Unlike the above-shown example of daily activity, here the data demonstrates various types of behavior. The period of time 701 preceding the fall evinces a small-amplitude behavior typical for daily activities, the period of time 702 corresponding to the fall is characterized by the dynamics of a higher complexity, with large ups and downs of the values of the acceleration's component, while the period of time 703 after the event evinces quiescence, indicating that the user does not move a lot during this time, e.g., suffering from an injury, being in shock, or an unconscious state.

The computational method 105 processes the data 103 by portions, in a moving window, and in doing so, for each portion of the data, it calculates the two-dimensional transform 107.

Figure 8:
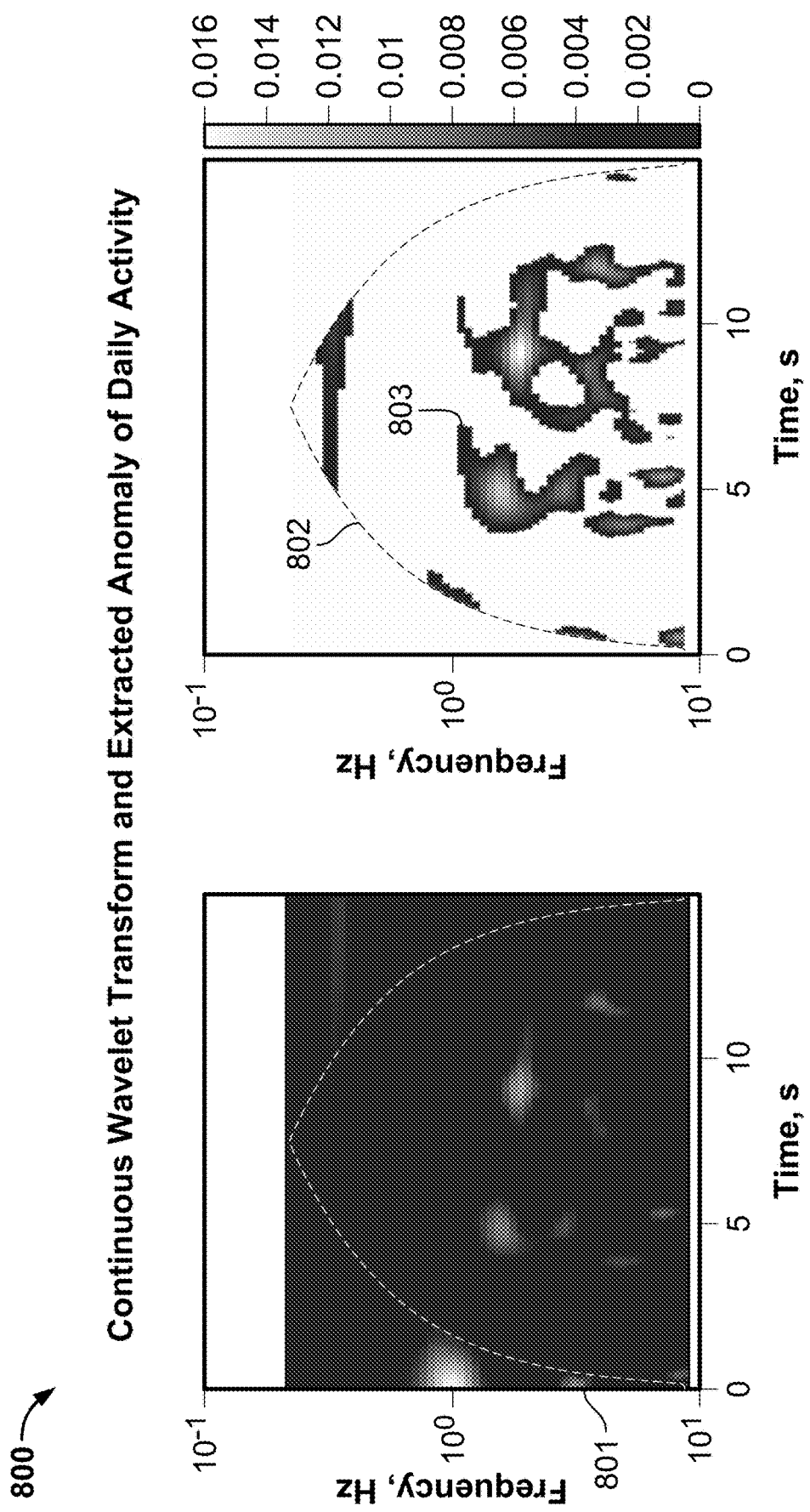
FIG. 8 shows an example of a two-dimensional transform of a portion of data reflecting a daily, non-fall-related activity (left) and an anomaly in the transform (right).

FIG. 8, on a 2D time-frequency plane 800, shows an example of a two-dimensional transform of a portion of data reflecting a daily, non-fall-related activity (left) and an anomaly in the transform (right).

In this example, the two-dimensional transform is the absolute square of a continuous wavelet transform 801 of a portion of the data 103 shown in FIG. 6. A curve 802 denotes the cone of influence, separating the area of reliable estimates beneath the cone from the area above the cone which contains edge effect artifacts. Of interest is an anomaly 803 extracted from the transform 801 and defined as the area where the transform's values are above a certain threshold (e.g., exceed 10% of the transform's maximum value).

As seen from FIG. 8, the anomaly 803 in the data 103 containing the period of daily activity is of an irregular shape, so that it is impossible to indicate a certain time range and/or a frequency range at which the data 103 would demonstrate a specific behavior. Besides, the maximum magnitude of the anomaly 803 is rather small compared to the values at the surrounding area below the threshold, not exceeding 0.016 (in relative units).

Figure 9:
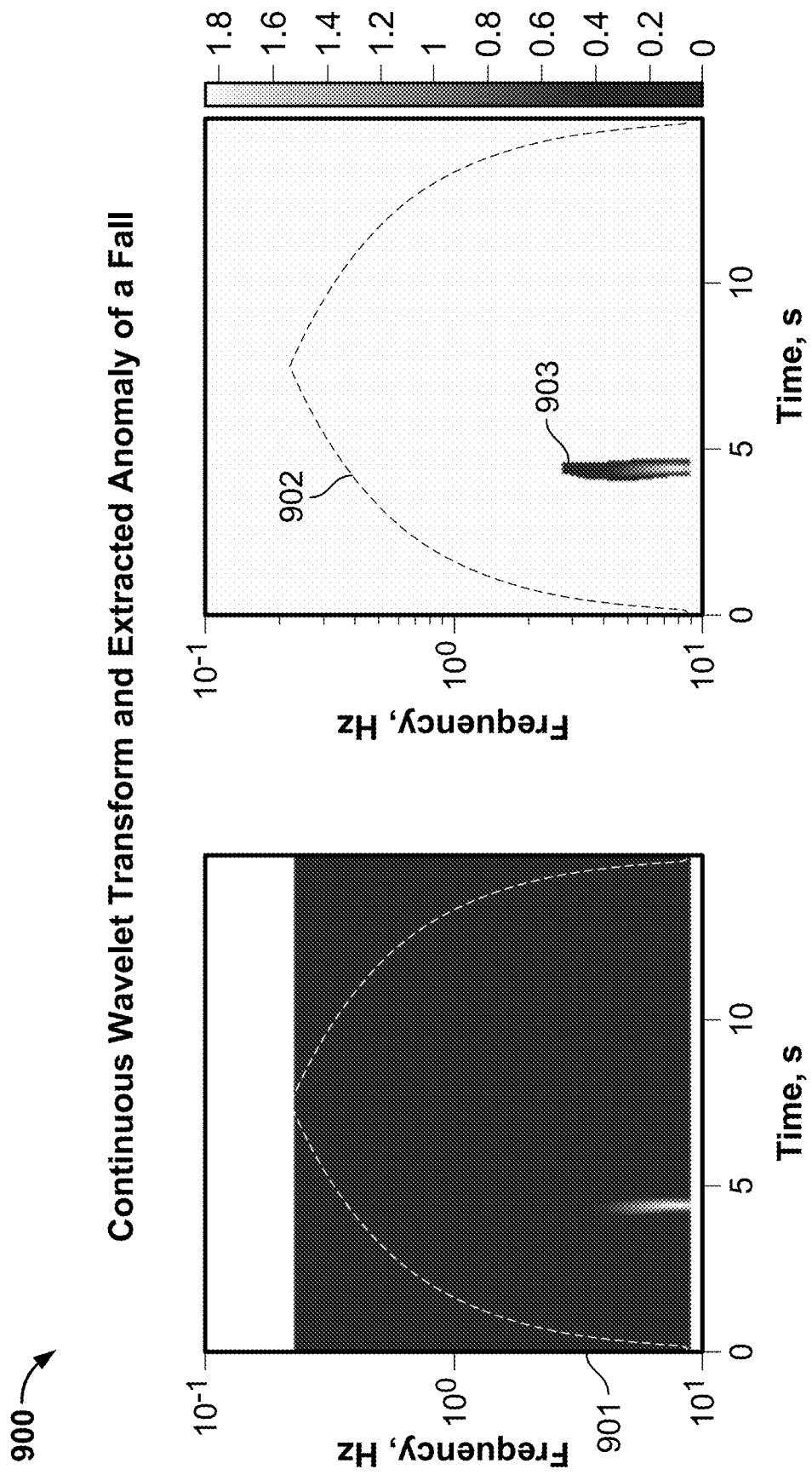
FIG. 9 shows an example of a two-dimensional transform of a portion of data containing a fall (left) and an anomaly in the transform (right).

As another example, FIG. 9, on a 2D time-frequency plane 900, shows a two-dimensional transform of a portion of data containing a fall (left) and an anomaly in the transform (right).

In this example, the two-dimensional transform is the absolute square of a continuous wavelet transform 901 of a portion of the data 103 shown in FIG. 7. A curve 902 has the same meaning as in FIG. 8, marking the cone of reliable estimates. Here of interest is an anomaly 903, which, unlike the anomaly 803, has distinct features: firstly, it is narrow, and it is strictly located around the time moment t 4.5 seconds corresponding to the very moment of the fall; secondly, it falls within a certain frequency range where the energy of the fall is mainly concentrated. Besides, the maximum magnitude of the anomaly 903 is essentially greater than the values at the surrounding points within the cone, exceeding 1.8 (in relative units).

In some implementations the transform 107 can be a two-dimensional data transform not necessarily based on wavelets.

For each anomaly A(t, f) (called, due to the underlying transform, a "T-anomaly") of the two-dimensional transform 107, the computational method 105 further calculates n properties 108.

As an example, with n=8, the computational method 105 can calculate the following properties:

the maximum magnitude $$M = \max_{t,f \in A} A,$$

the time range $$\Delta t = \max_{t \in A} t - \min_{t \in A} t,$$

the frequency range $$\Delta f = \max_{f \in A} f - \min_{f \in A} f,$$

the area $S = \Sigma_{t,f \in A} 1,$ the total energy $E = \Sigma_{t,f \in A} A^2,$ the center in time $$c_t = \frac{\sum_{t,f \in A} At}{\sum_{t,f \in A} A},$$

the center in frequency $$c_f = \frac{\sum_{t,f \in A} At}{\sum_{t,f \in A} A}$$

and the fractal dimension $$D = \underset{t,f \in A}{\text{box}} A,$$

where the function box(·) represents an algorithm for calculating the fractal dimension of a two-dimensional set. As an example, such an algorithm may be based on box-counting.

In some implementations for the extracted anomalies A(t, f)'s the computational method 105 can calculate functions of these properties, e.g., a logarithm of the energy.

In some implementations for the extracted anomalies A(t, f)'s the computational method 105 can calculate other properties, not necessarily the ones shown above.

In some implementations for the extracted anomalies A(t, f)'s the computational method 105 can use a different number of properties, not necessarily n=8.

For the n calculated properties the computational method 105 compiles all possible k-dimensional combinations, running k from 1 to n. For a fixed k the number of all possible combinations is thus $$\frac{n!}{(n-k)!k!}.$$

As an example, under n=8 for k=1 the computational method 105 makes 8 one-property combinations, for k=2 it makes 28 two-property combinations, for k=3 it makes 56 three-property combinations, and so on, until k=8 when it makes only one eight-property combination that includes all n of the calculated properties.

The Training Mode

In the training mode, while processing the data 103 provided as a finite dataset of N data portions of length L seconds each, the computational method 105 passes over the data with a moving window by (i) calculating a two-dimensional transform 107 of a given portion of the data and further (ii) extracting an anomaly from it and calculating the n properties 108, and with every new portion of the data, referred to as an observation, it fills out n tables of state spaces 110 (called "T-tables" because of the underlying transform). In doing so, for a fixed $k^{th}$ table of state spaces the computational method 105 adds an appropriate new k-dimensional row to each of the $$\frac{n!}{(n-k)!k!}$$

tables of observations.

Figure 10:
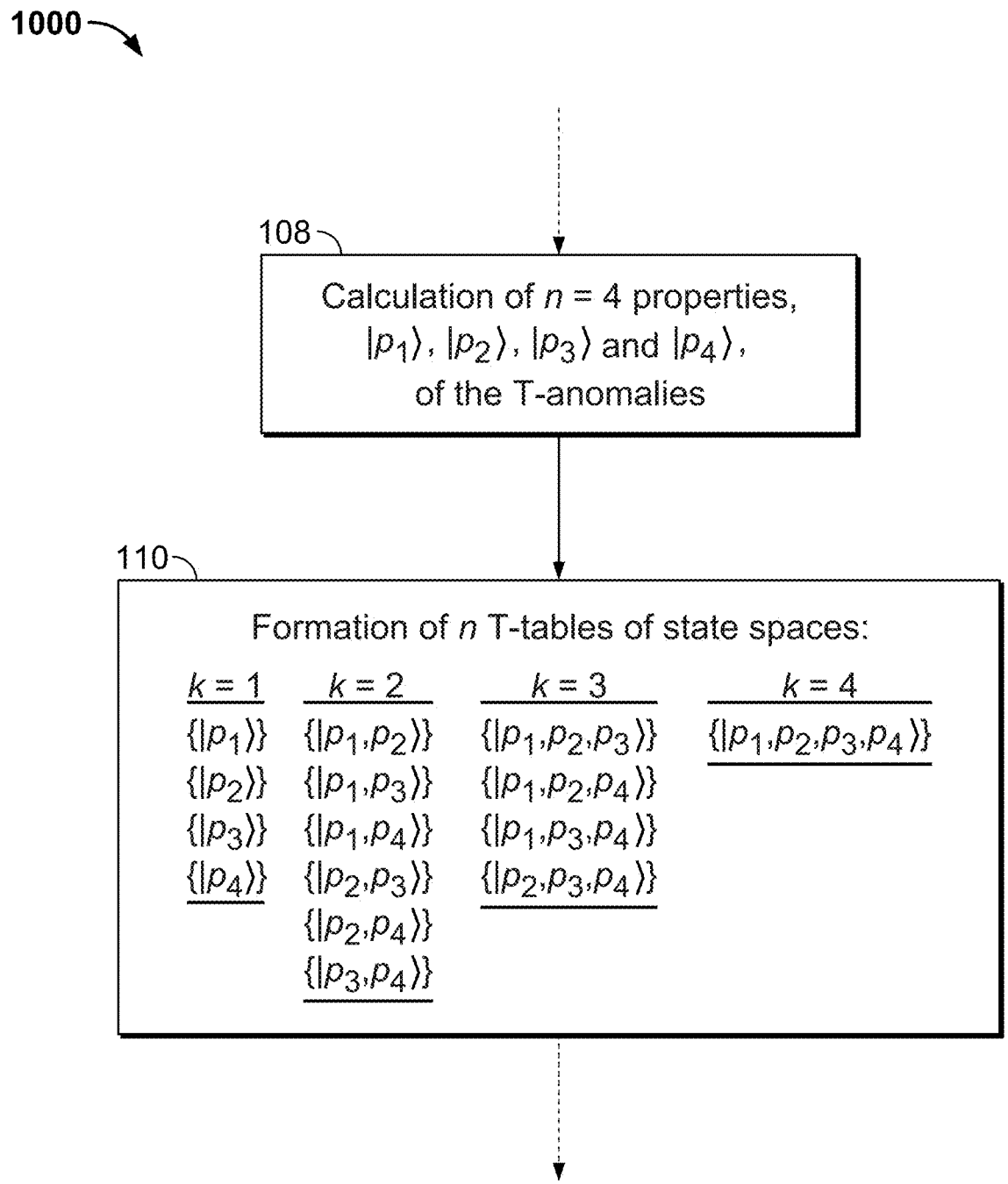
FIG. 10 illustrates the initial performance of the computational method of a fall detection system in the training mode.

FIG. 10, on a process flowchart 1000, illustrates the initial performance of the computational method 105 of the fall detection system 100 in the training mode. The method calculates n different properties of an anomaly and then forms all possible k-dimensional combinations of these properties (k∈[1, n]) that determine the corresponding k-dimensional state spaces.

In this example, the initial formation of the T-tables 110 for n=4 properties, denoted as $|p_j\rangle$'s, j=$\overline{1,4}$, previously calculated in the block 108 for the very first portion of the data 103, or for the observation at $t_i$ under i=1, is shown. Because k runs from 1 to 4, there are $$\frac{4!}{(4-1)!1!} = 4 \quad \text{(i)}$$

one-property combinations, from $|p_1\rangle t_i$ to $|p_4\rangle t_i$, forming the first table of state spaces $\{|p_{j_1}\rangle\}$'s, $$\frac{4!}{(4-2)!2!} = 6 \quad \text{(ii)}$$

two-property combinations, from $|p_1,p_2\rangle t_i$ to $|p_3,p_4\rangle t_i$, forming the second table of state spaces $\{|p_{j_1},p_{j_2}\rangle\}$'s, $$\frac{4!}{(4-3)!3!} = 4 \quad \text{(iii)}$$

three-property combinations, from $|p_1,p_2,p_3\rangle t_i$ to $|p_2,p_3,p_4\rangle t_i$, forming the third table of state spaces $\{|p_{j_1}, p_{j_2},p_{j_3}\rangle\}$'s and $$\frac{4!}{(4-4)!4!} = 1 \quad \text{(iv)}$$

four-property combination $|p_1,p_2,p_3,p_2\rangle t_i$ forming the last T-table of the single state space $\{|p_1,p_2,p_3,p_4\rangle\}$.

After the initial formation 110 has been completed, every of then T-tables contains, respectively for k running from 1 to $$n, \frac{n!}{(n-k)!k!}$$

tables of observations with only one k-dimensional entry, or row, each, because so far only one portion of the data 103, or only one observation, has been processed.

Figure 11:
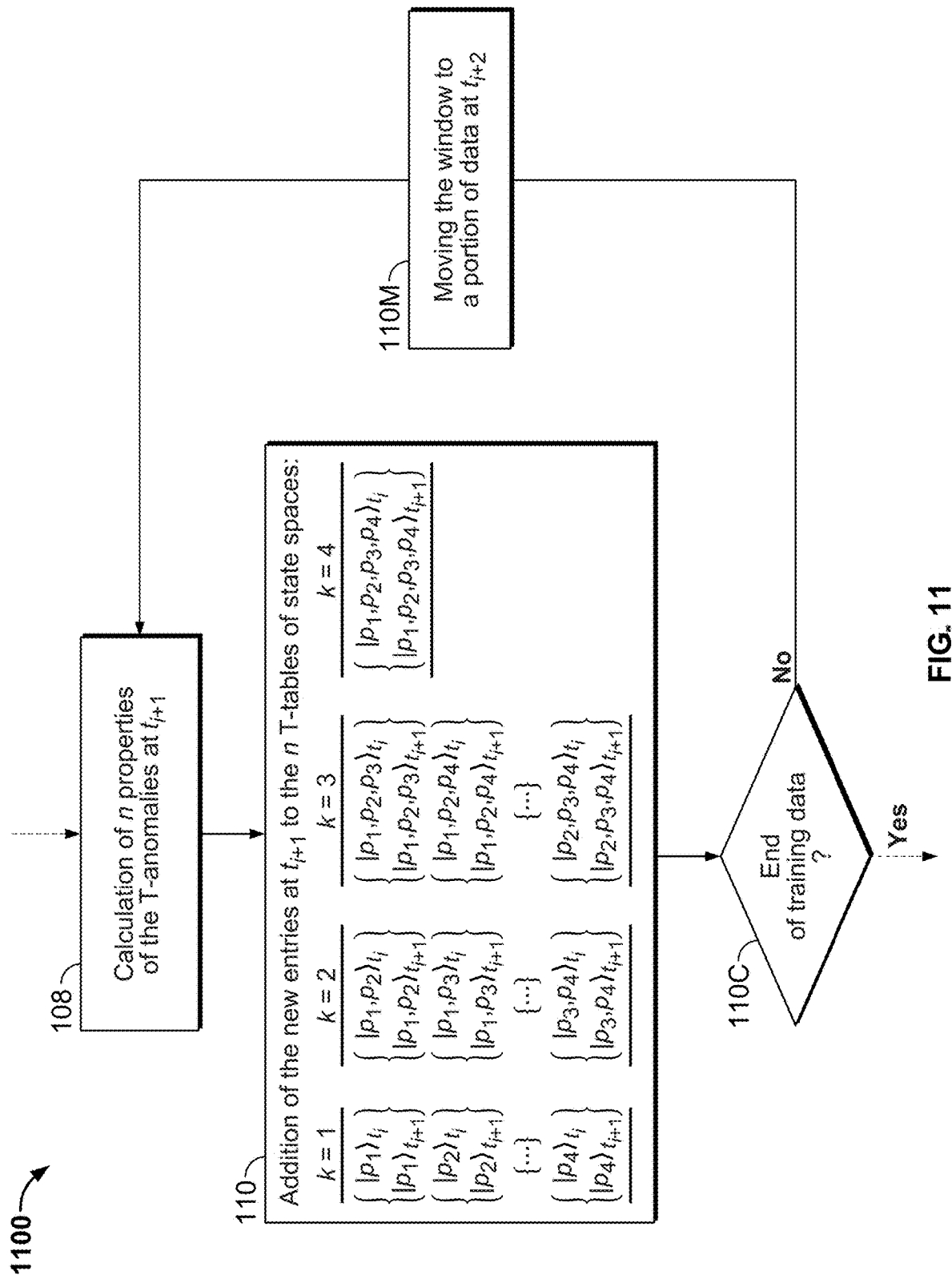
FIG. 11 illustrates the full performance of the computational method of a fall detection system in the training mode.

FIG. 11, on a wider process flowchart 1100, illustrates the full performance of the computational method 105 of the fall detection system 100 in the training mode. The available data is processed by portions, in a moving window. At every time moment the n different properties of a current anomaly are calculated and their all possible k-dimensional combinations, k∈[1, n], are added as new rows to the corresponding tables of state spaces.

In particular, as a continuation of the example from FIG. 10, FIG. 11 shows the filling out of the n=4 T-tables 110 with the properties of the subsequent observations 108 while the computational method 105 is processing the whole data 103 in a cycle 110C using a moving window 110M, until all the N observations are processed. As soon as a new portion of the data 103 corresponding to the time moment $t_{i+1}$ has been obtained, its two-dimensional transform 107 has been calculated and the corresponding T-anomaly has been extracted and its n=4 properties $|p_1\rangle t_{i+1}$ to $|p_4\rangle t_{i+1}$ have been quantified 108, the computational method 105 adds (i) an appropriate new one-dimensional entry $|p_{j_1}\rangle t_{i+1}$ to every of the four one-property tables of observations within the first table of state spaces, thus enlarging the corresponding one-property state spaces $\{|p_{j_1}\rangle\}$'s, (ii) an appropriate new two-dimensional entry $|p_{j_1},p_{j_2}\rangle t_{i+1}$ to each of the six two-property tables of observations within the second table of state spaces, thus enlarging the corresponding two-property state spaces $\{|p_{j_1},p_{j_2}\rangle\}$'s, (iii) an appropriate new three-dimensional entry $|p_{j_1},p_{j_2},p_{j_3}\rangle t_{i+1}$ to each of the four three-property tables of observations within the third table of state spaces, thus enlarging the corresponding three-property state spaces tip $\{|p_{j_1},p_{j_2},p_{j_3}\rangle\}$'s, and (iv) the only possible new four-dimensional entry $|p_{j_1},p_{j_2},p_{j_3}\rangle t_{i+1}$ to the single four-property table of observations within the fourth table of state spaces, thus enlarging the unique four-property state space $\{|p_1,p_2,p_3,p_4\rangle\}$.

By processing the data 103 in the cycle 110C using the moving window 110M, for every of the n T-tables the computational method 105 produces, respectively for k running from 1 to $$n, \frac{n!}{(n-k)!k!}$$

tables or observations, each of which contains N k-dimensional entries, or rows.

As a result, for every fixed pair of the parameters k and l, with k running from 1 to n and l running from 1 to $$\frac{n!}{(n-k)!k!},$$

there appears a table of operations on which a machine learning model can be built; it is called a "T-model" because it is based on the data transform 107.

After the computational method 105 has processed the data 103 with all N observations and has determined the state spaces reflecting the user's activity in terms of the corresponding properties, each of the tables of observations gets divided into two parts: a training dataset of length O observations and a testing dataset of length P observations, so that O+P=N. As an example, the separation in the two parts can be performed by assuming $$O = P = \frac{N}{2}$$

(for an even N) or $$O = \frac{N-1}{2}, P = \frac{N-1}{2} + 1 \text{ (for an odd } N\text{)}.$$

For every training dataset the machine learning models 111 are taught 112 by separating the O observations into two clusters using a statistical learning method.

Figure 12:
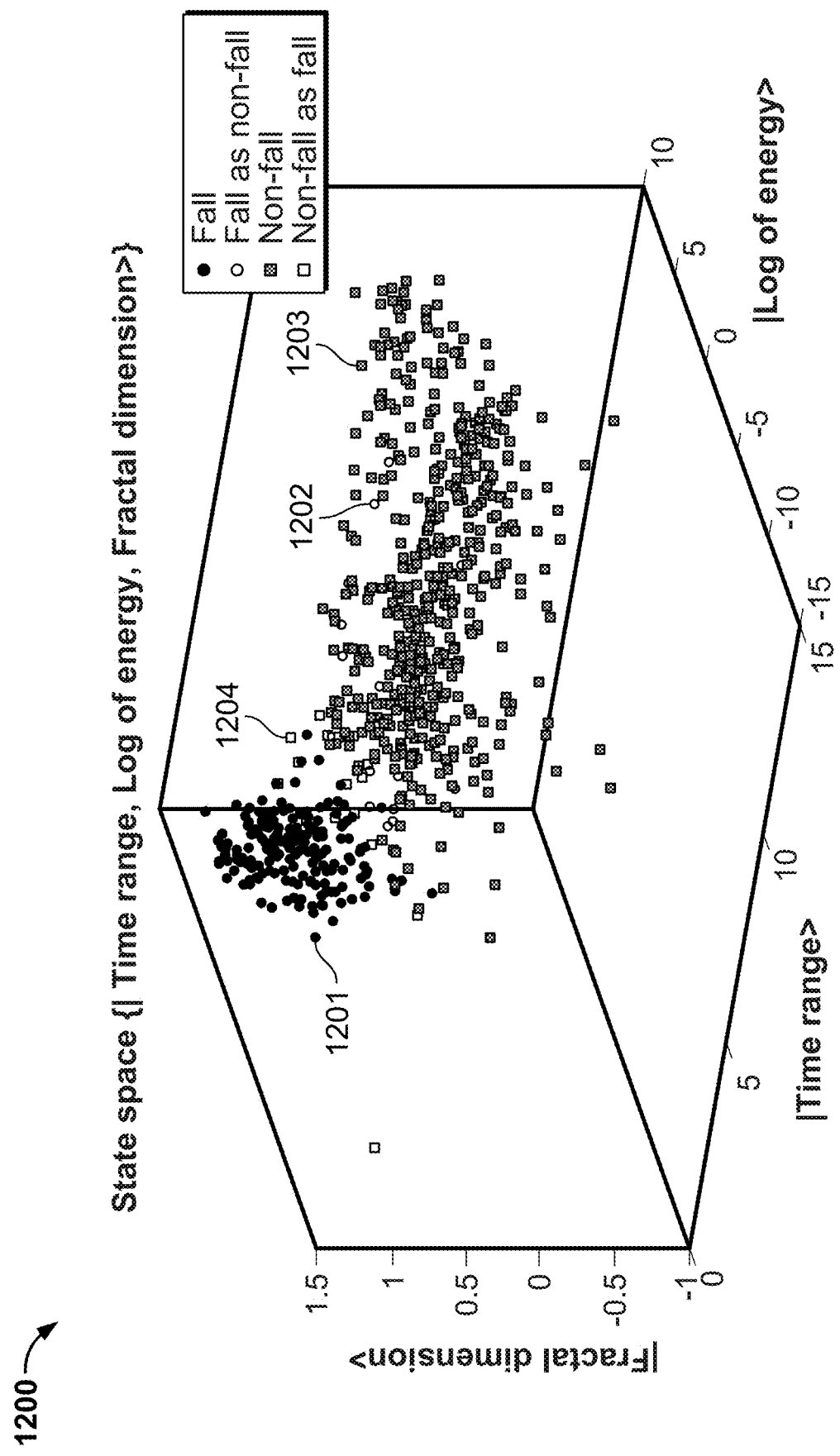
FIG. 12 shows an example of a three-dimensional state space formed after the application of the computational method in the training mode.

FIG. 12 shows an example of a state space 1200 formed after the application of the computational method 105 in the training mode. Each point represents a combination of properties quantifying an anomaly found in the data after processing. The entire cloud of points is separated into two big clusters, one representing falls and the other representing activities of daily living.

In this example, the separation of a training dataset is performed in a three-dimensional state space $\{|p_1,p_2,p_3\rangle\}$, where the property $|p_1\rangle$ quantifies the time range, the property $|p_2\rangle$ quantifies the natural logarithm of the energy, while the property $|p_3\rangle$ quantifies the fractal dimension. The filled circles 1201 represent falls which are correctly classified as falls, the hollow circles 1202 represent falls falsely classified as non-fall-related daily activities, the filled squares 1203 represent non-fall-related daily activities truly classified as such, whereas the hollow squares 1204 represent daily activities falsely classified as falls.

Because, as this is clearly reflected in the portions of the data 103 shown in FIG. 6 and FIG. 7 and further in the corresponding anomalies shown in FIG. 8 and FIG. 9, the user's movement under falls essentially differs from daily activity in the absence of falls, one of the separated clusters can be attributed to falls, while the other to a daily, non-fall-related activity.

In some implementations the training 112 of the machine learning models 111 can be performed by separating the O observations into a larger number of clusters, not necessarily two. In such an implementation a greater number of the user's activities, not only falls and non-falls, can be identified, that is non-falls can further be identified as particular daily activities.

In some implementations the statistical learning method used for the training 112 of the machine learning models 111 can be a support vector machine method.

For every testing dataset the machine learning models 111 are validated 113 by making classifications for each of the P observations and by comparing the results of the classification with the true responses. This produces a fall-related false positive rate $$\frac{\varphi}{2\Delta},$$

a fall-related false negative rate $$\frac{\delta}{2\Phi},$$

and a fall-related total false rate $$\frac{\varphi}{2\Delta} + \frac{\delta}{2\Phi},$$

where $\Delta$ is the number of daily activities, $\Phi$ is the number of falls, $\Delta+\Phi=P$, while $\varphi \in [0,\Delta]$ is the number of observations within the subset of $\Delta$ daily activities classified as falls, and $\delta \in [0,\Phi]$ is the number of observations within the subset of $\Phi$ falls classified as daily activities.

As a result, for every fixed pair of the parameters k and l, with k running from 1 to n and l running from 1 to $$\frac{n!}{(n-k)!k!},$$

the corresponding machine learning transform-based model, or the T-model, is attributed a fall-related total false rate that quantifies the model's classification accuracy.

The minimization over all the fall-related total false rates yields the optimal machine learning model 114 (the "optimal T-model") producing the most accurate classification of falls and daily activities.

The Execution Mode

In the execution mode, while processing the data 103 provided as a continuous stream for the duration of monitoring, the computational method 105 takes a new portion of the data, calculates its two-dimensional transform 107, extracts an anomaly and calculates the n properties 108, and sends the output to the machine learning models 111.

The optimal machine learning model 114 classifies the obtained n-dimensional vector of properties by addressing it to one of the two clusters, thus producing a decision whether it was a fall or an activity of daily living.

Multiple-Device Systems

In some implementations a system for determining if a user has fallen may comprise multiple wearable devices, and thus have multiple sensors that jointly produce multi-sensor data.

Figure 13:
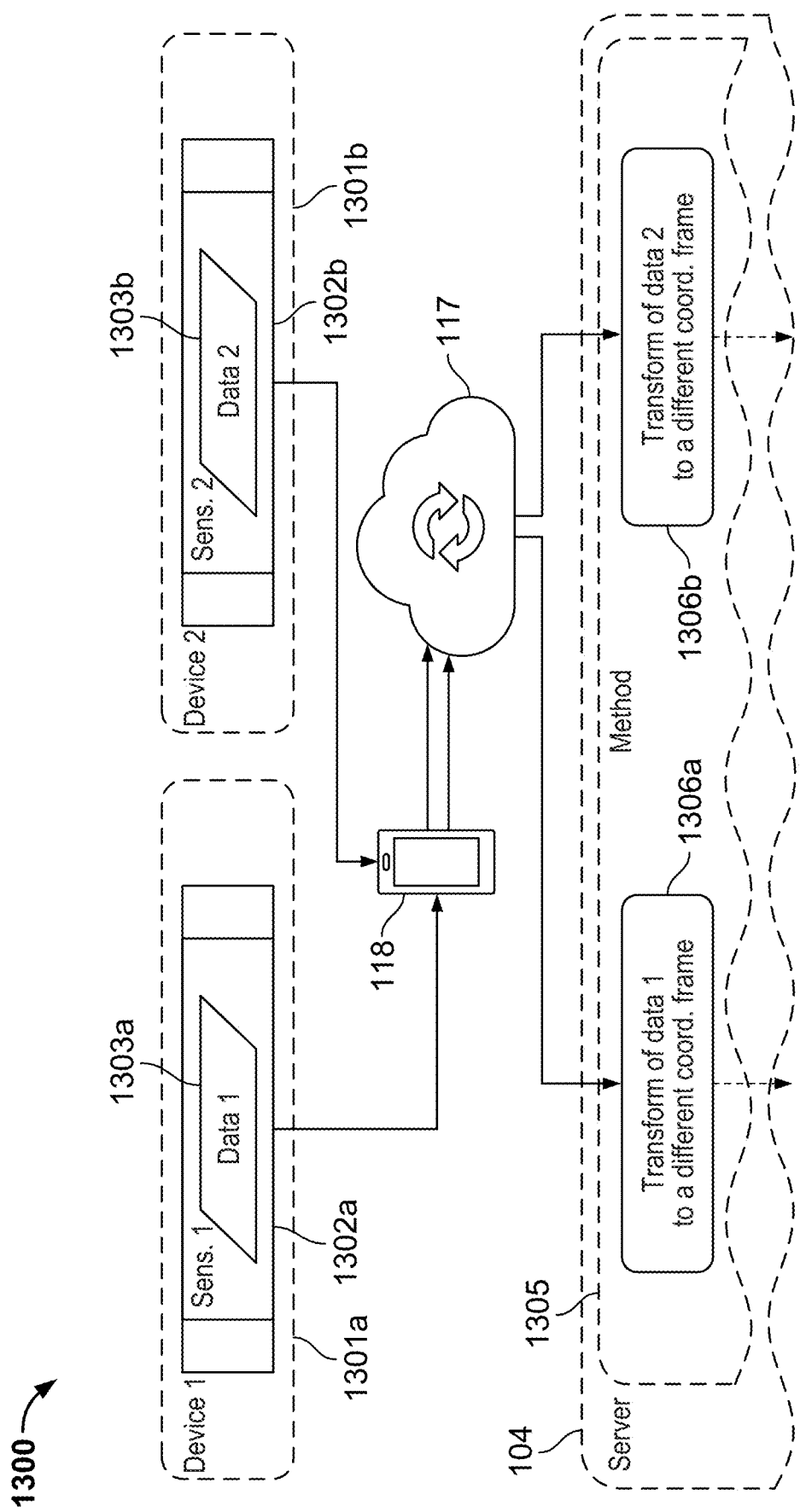
FIG. 13 shows a two-device fall detection system.

FIG. 13 shows a two-device fall detection system. The two one-sensor time series recorded by the client are transmitted to the server to be processed by a computational method. Specifically, FIG. 13 shows a part of a system 1300, implemented as a client-server solution, with two wearable devices 1301a and 1301b containing motion sensors 1302a and 1302b, respectively, that jointly produce two-sensor data 1303a,b.

The two devices 1301a and 1301b jointly represent the client that communicates with the server 104, which runs a computational method 1305, through a network 117 via a smartphone 118.

Figure 14:
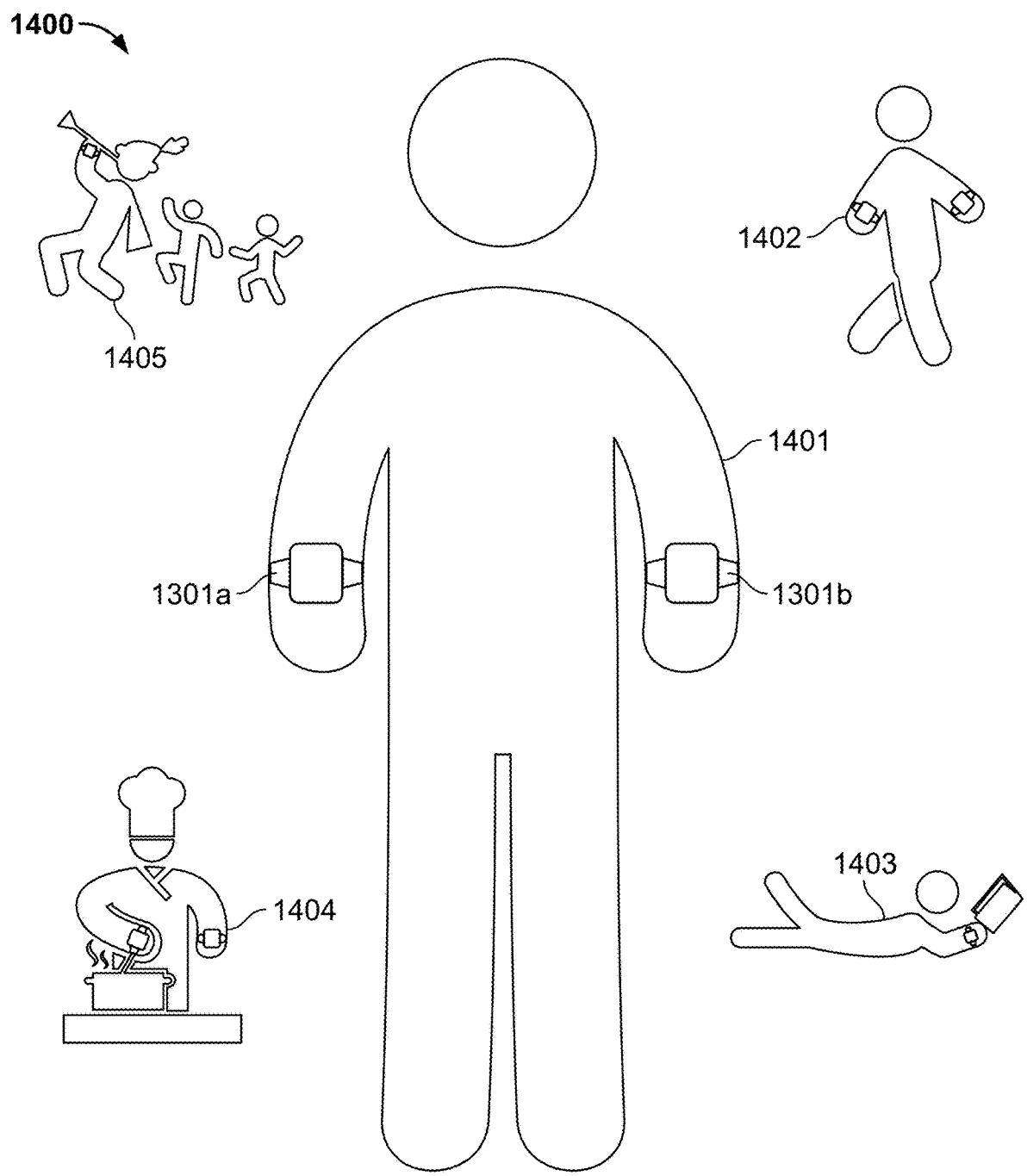
FIG. 14 shows a placement of two wearable devices on a human body and several examples of activities of daily living.

An example of functioning of the system 1300 is shown in FIG. 14, illustrating different types of the user's activities 1400. The user 1401 places the two wearable devices 1301a and 1301b on the wrists and goes about daily life, e.g., walking 1402, lying 1403, cooking 1404, playing 1405 etc., while the devices' sensors 1302a and 1302b collect the two sensor time series 1303a and 1303b, respectively.

In practice the multiple wearable devices can be placed on other parts of the body of the user 1401, not necessarily on the wrists.

Unlike a single-device system, in a multiple-device system a computational method can process all the measured data either jointly, treating them as a single entity—multi-sensor data, or separately, treating them as several independent entities.

Multiple-Device Coherence-Based System

Figure 15:
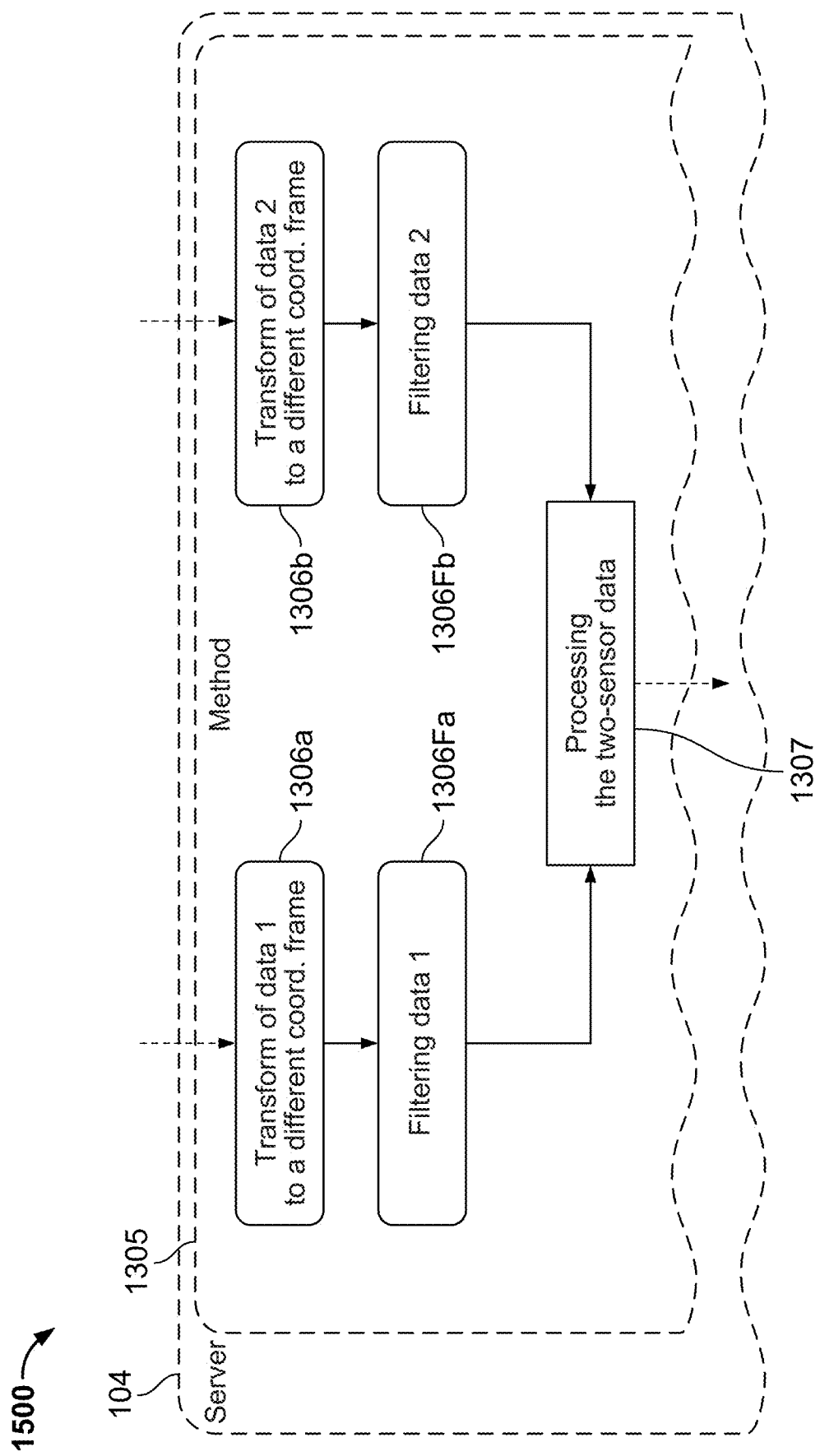
FIG. 15 shows an implementation of a two-device fall detection system when the computational method jointly processes the two-sensor data, after these have been optionally preprocessed and filtered.

An example of the joint consideration of the data from multiple motion sensors is shown in FIG. 15, which, on a flowchart 1500, illustrates the beginning of the processing of the two-sensor data 1303a,b by the computational method 1305. Each of the single-sensor data are preliminarily transformed from an original sensor-related coordinate frame to a special coordinate frame by the corresponding block 1306a or 1306b, respectively, and then the transformed data is filtered by the corresponding block 1306Fa or 1306Fb. Afterwards the two transformed and filtered single-sensor data are submitted for joint processing by the block 1307.

In some implementations the filtering may include three steps. At the first step, each one-sensor time series of the multi-sensor data, provided either directly from the corresponding motion sensor or additionally preprocessed to a special coordinate frame, is processed using a two-dimensional transform that preserves time as the first axis. At the second step, the result of the two-dimensional transform is averaged along the second, non-time axis, making the output one-dimensional. At the third step, for the one-dimensional result of the previous averaging the first derivative in time is calculated, making the output stationary.

Figure 16:
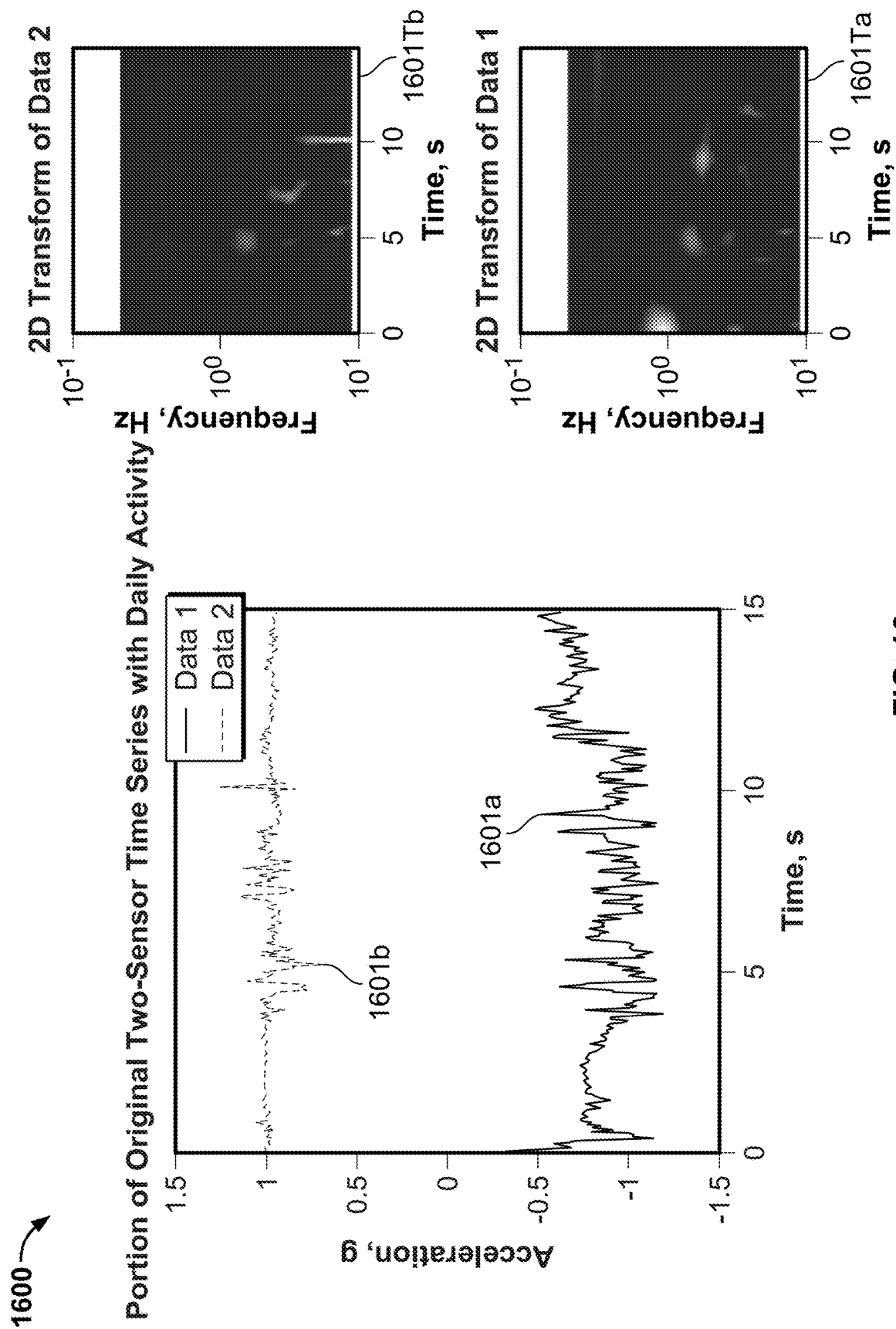
FIG. 16 shows a 15-seconds-long portion of one component of a 3D two-sensor time series of accelerations recorded by two wearable devices (left) and their two-dimensional transforms (right) when the user performs activities of daily living.

As an example, FIG. 16, on a 2D plot and time-frequency plane 1600, shows a portion of the original two-sensor data containing a period of daily activity 1601a,b (left) and two data transforms of each of the one-sensor data 1601Ta,b (right).

Figure 17:
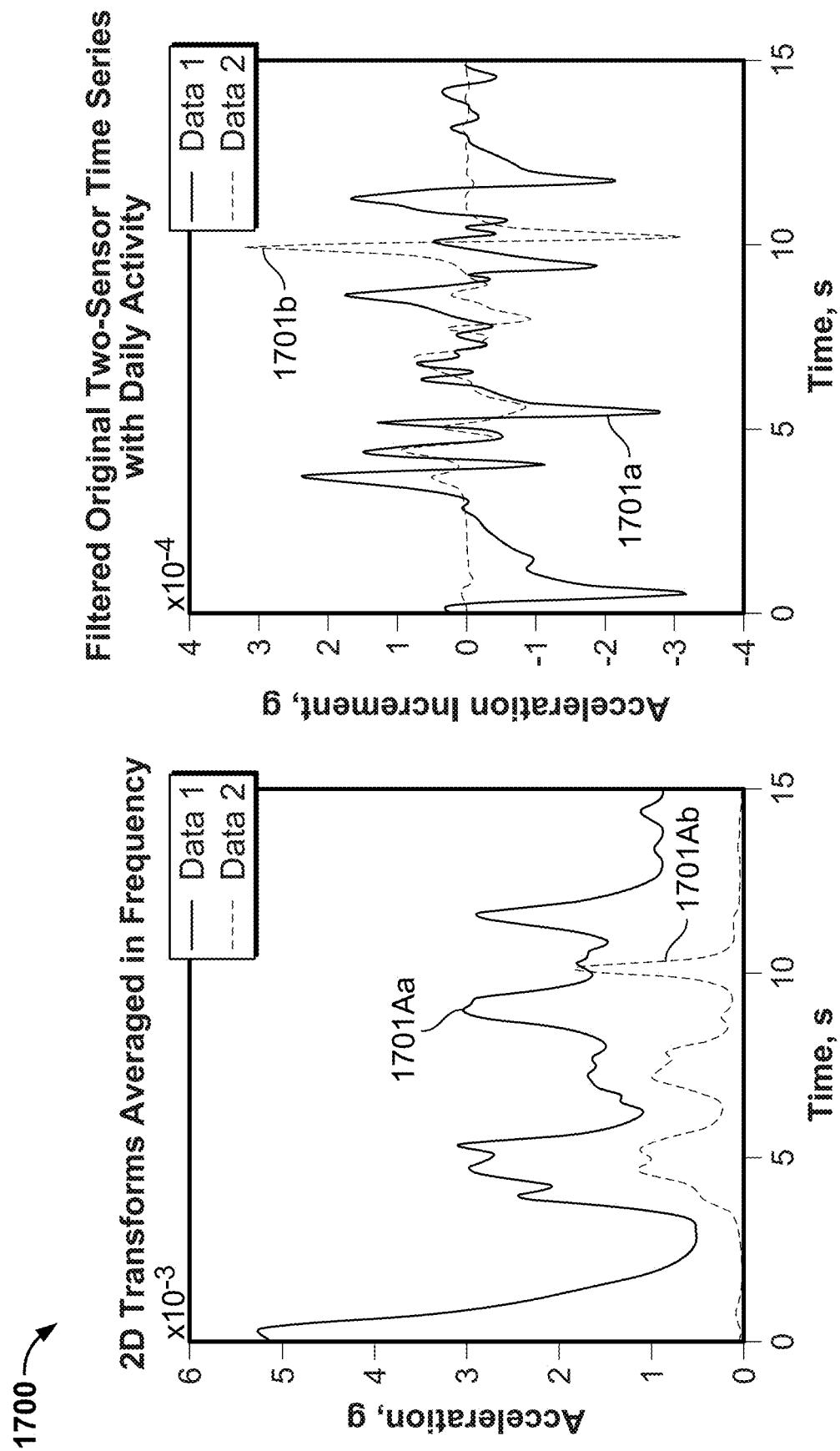
FIG. 17 shows the data from on the right side in FIG. 16 after they have been averaged in frequency (left) and differentiated in time (right).

As a further illustration of the example from FIG. 16, FIG. 17, on a 2D plot 1700, shows the transforms averaged in frequency 1701Aa,b (left) and the ultimate result of the filtering 1701a,b after calculating the first derivative in time (right). In this example the 2D data transforms 1601Ta,b, are calculated as the absolute squares of continuous wavelet transforms of the data 1601a,b.

Figure 18:
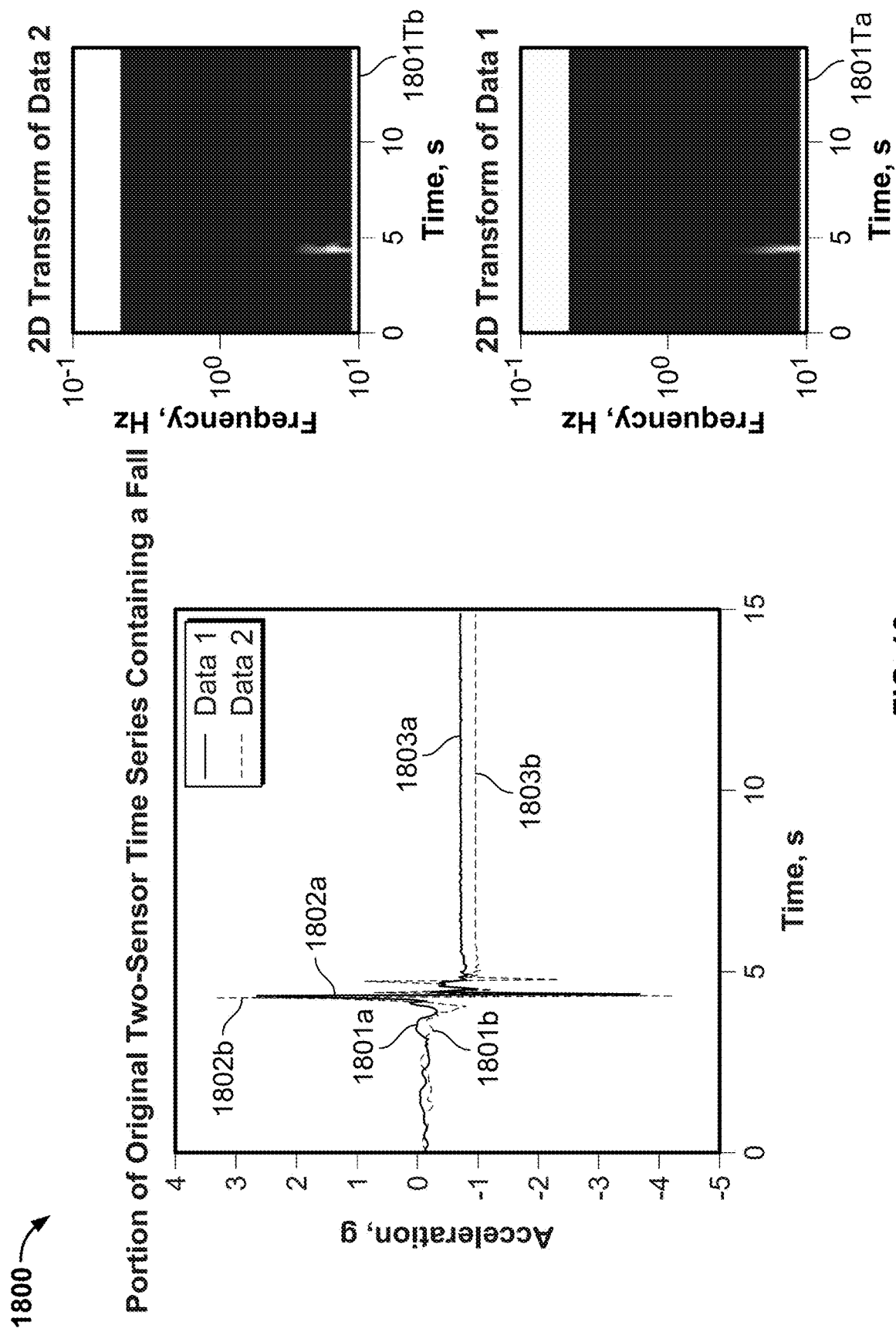
FIG. 18 shows a 15-seconds-long portion of one component of a 3D two-sensor time series of accelerations recorded by two wearable devices (left) and their two-dimensional transforms (right) when the user commits a fall.

Another example of the original two-sensor data 1303a,b, now containing a fall, is shown in FIG. 18. A portion of the original two-sensor data containing a fall 1802a,b preceded by a period of normal activity 1801a,b and followed by a period of quiescence 1803a,b (left), along with two data transforms of each of the one-sensor data 1801Ta,b (right), are shown as a 2D plot and time-frequency plane 1800.

Figure 19:
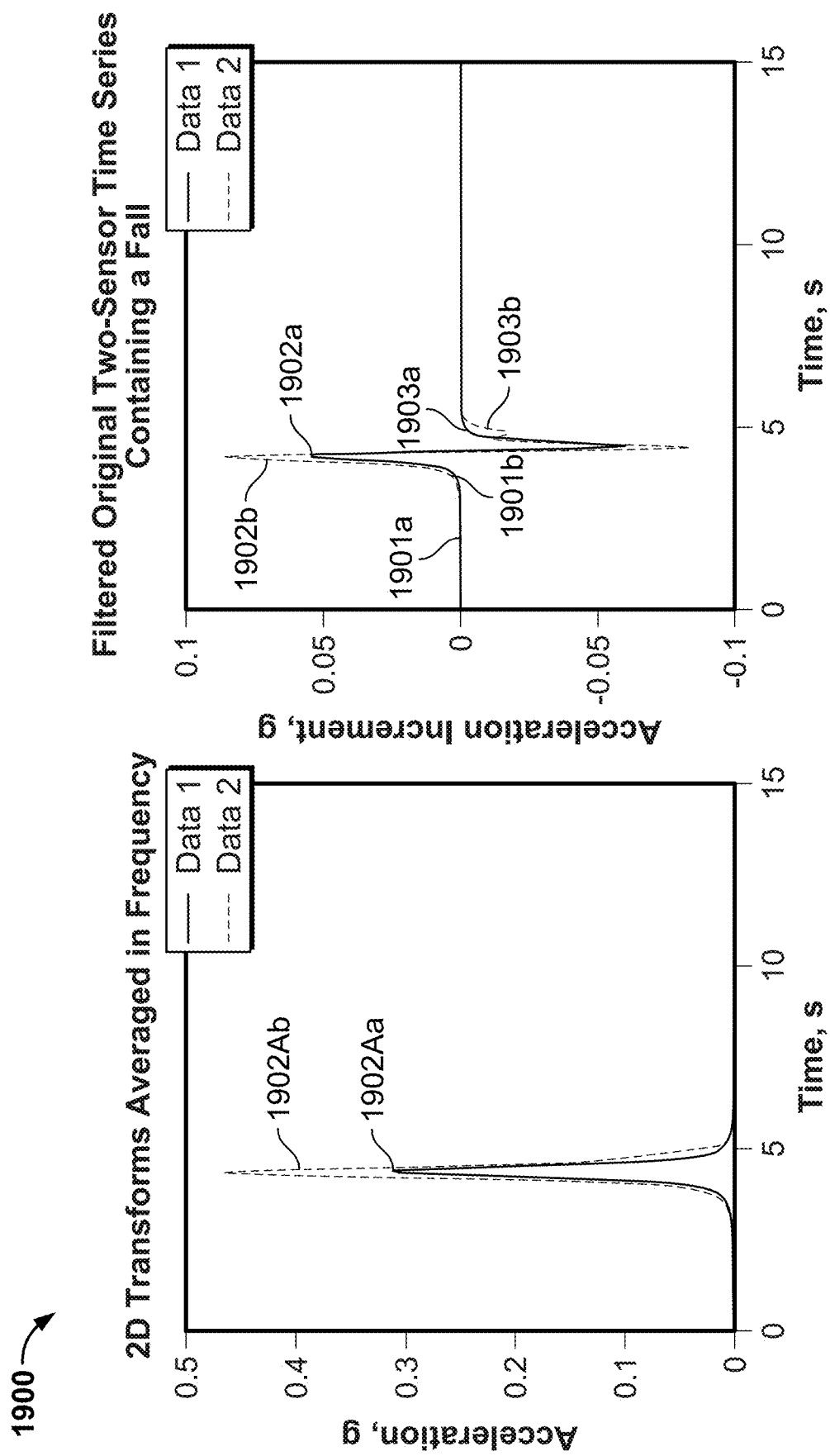
FIG. 19 shows the data from FIG. 18, right, after they have been averaged in frequency (left) and the first derivative in time has been calculated (right).

As a further illustration of the example from FIG. 18, FIG. 19 shows those data after applying the filtering procedure. The transforms averaged in frequency 1902Aa,b (left) and the ultimate result of filtering after calculating the first derivative in time (right), with the period of normal activity 1901a,b, the moment of the fall 1902a,b and the period of quiescence 1903a,b, are shown as a 2D plot 1900.

In some implementations the block of the joint processing 1307 can involve the calculation of a wavelet-based total coherence field $$C(f, b) = \left(\prod_{l=1}^{p} \lambda_l(f, b)\right)^{\frac{1}{p}}$$

between all the one-sensor time series of the multi-sensor data, where $\lambda_l(f, b)$'s are the maximum eigenvalues of the corresponding matrices $$c_l(f, b) = \frac{S^*_{xx}(l) S^{-1}_{xx} S_{xx}(l)}{S_{x^{(l)} x^{(l)}}}$$

at the frequency f and at the time shift b. Here $S_{x^{(l)} x^{(l)}}(f, b)$ is the 1×1 matrix (i.e., a real number) of the wavelet-based power spectrum of the one-sensor data $x^{(l)}$ at the frequency f and at the time b; $S_{xx^{(l)}}(f,b)$ is the (p−1)×1 matrix of the wavelet-based cross spectra between the one-sensor data $x^{(l)}$ and the multi-sensor data with the excluded lth component $x = \{x^{(1)}, \ldots, x^{(l-1)}, x^{(l+1)}, \ldots, x^{(p)}\}$; $S_{xx}^{-1}(f,b)$ is the inverse of the (p−1)×(p−1) matrix of the wavelet-based power (for i=j) or cross (for i≠j) spectra between the one-sensor data x (i) and $x^{(j)}$ from x, while $S_{xx^{(l)}}*(f,b)$ is the 1×(p−1) matrix conjugate transposed to $S_{xx^{(l)}}(f, b)$.

Figure 20:
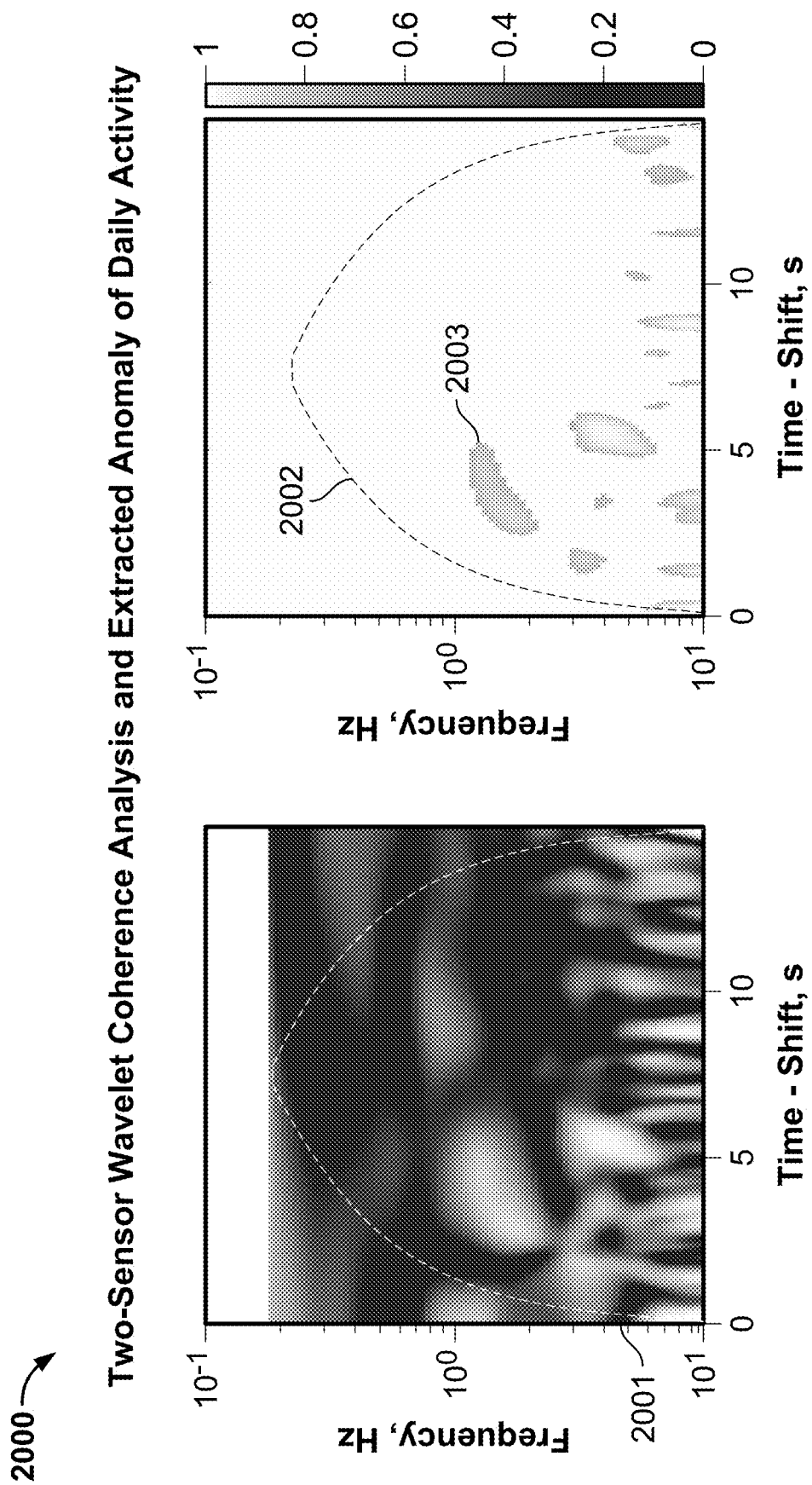
FIG. 20 shows an example of a wavelet-based total coherence field of the filtered two-sensor data from FIG. 17 (left) and an anomaly where the field's values are above a threshold (right).

As an example, FIG. 20, on a 2D time-frequency plane 2000, shows a wavelet-based total coherence field 2001 between the filtered two-sensor data corresponding to a daily activity from FIG. 17, calculated by the block 1307, as well as a cone of influence 2002

Figure 21:
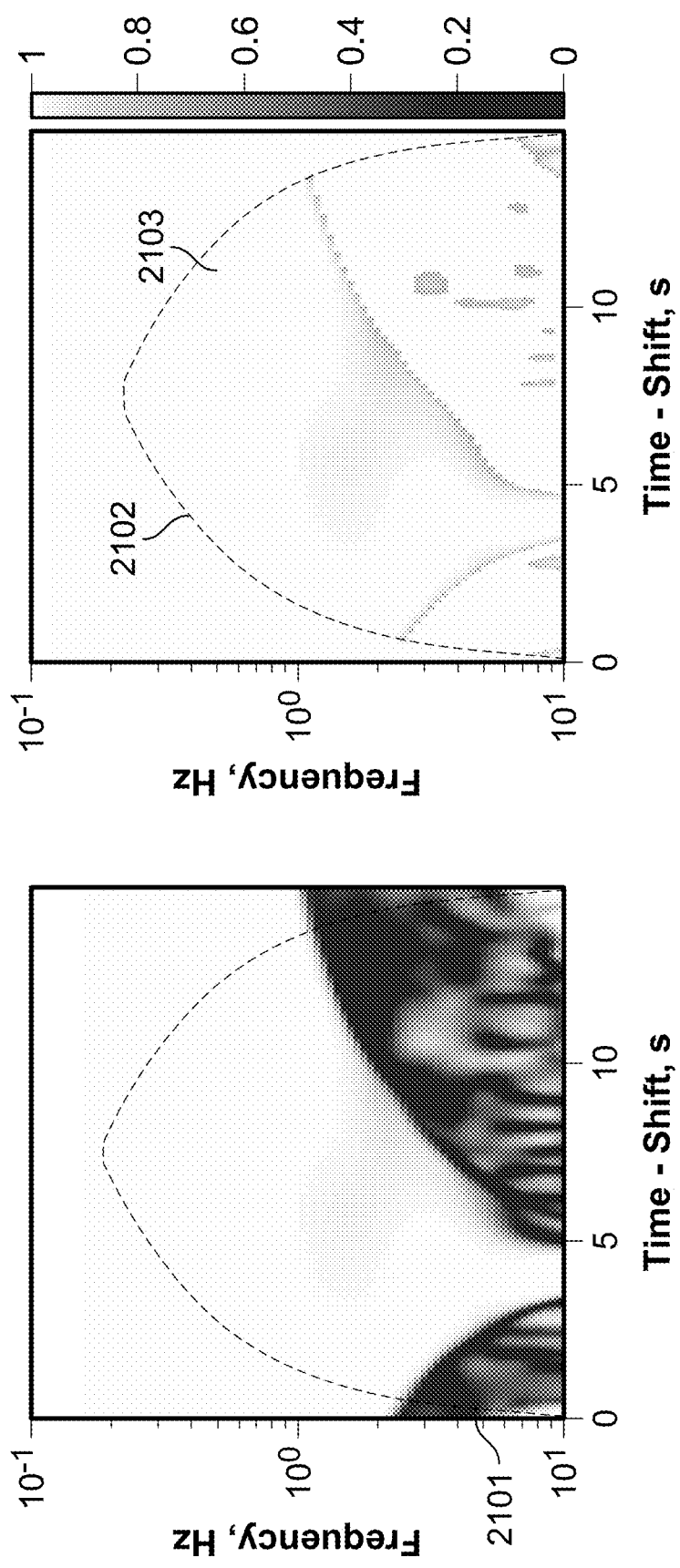
FIG. 21 shows an example of a wavelet-based total coherence field of the filtered two-sensor data from FIG. 19 (left) and an anomaly where the field's values are above a threshold (right).

As another example, FIG. 21, on a 2D time-frequency plane 2100, shows a similar wavelet-based total coherence field 2101 between the filtered two-sensor data containing a fall from FIG. 19, calculated by the block 1307, and a cone of influence 2102 for it.

Unlike a two-dimensional data transform underlying the computational method in a single-device system, e.g., as in the block 107 of the single-device system 100, where the transform's absolute squares can take arbitrary values, the values of a total coherence field vary in the interval from 0 to 1, where the value 0 indicates that at a given time moment there are no common frequencies in the multi-sensor time series, while the value 1 means that the multi-sensor data is perfectly coherent, or synchronized, at a given frequency. This is clearly seen by comparing FIG. 20 and FIG. 21: the anomalies corresponding to the activity of daily living are sporadic 2003, showing that the dynamic of different parts of the user's body is mostly asynchronized, while the anomalies appearing under the fall highlight a particular time-frequency area 2103, indicating that the motions of different parts of the body are highly determined by a single coherent force.

The architecture of the remaining part of a multiple-device fall detection system, namely of its computational method and its machine learning models, is the same as in a single-device transform-based system, e.g., as in the system 100.

Within the same example of the joint processing based on calculating a total coherence field, in the training mode the computational method 1305 determines anomalous areas (called "C-anomalies") where the total coherence is above a threshold, calculates properties of the anomalies, and fills out the corresponding tables of state spaces (called "C-tables"). In turn, the machine learning models (the "C-models") get trained and validated, and the subsequent minimization over the fall-related total false rates ultimately produces the optimal coherence-based machine learning model (the "optimal C-model").

In the execution mode the computational method 1305 takes a new portion of the continuous stream, processes it jointly as a single entity, extracts an anomaly, calculates its properties, and sends the output to the optimal C-model for classification.

Multiple-Device Voting-Based System

Figure 22:
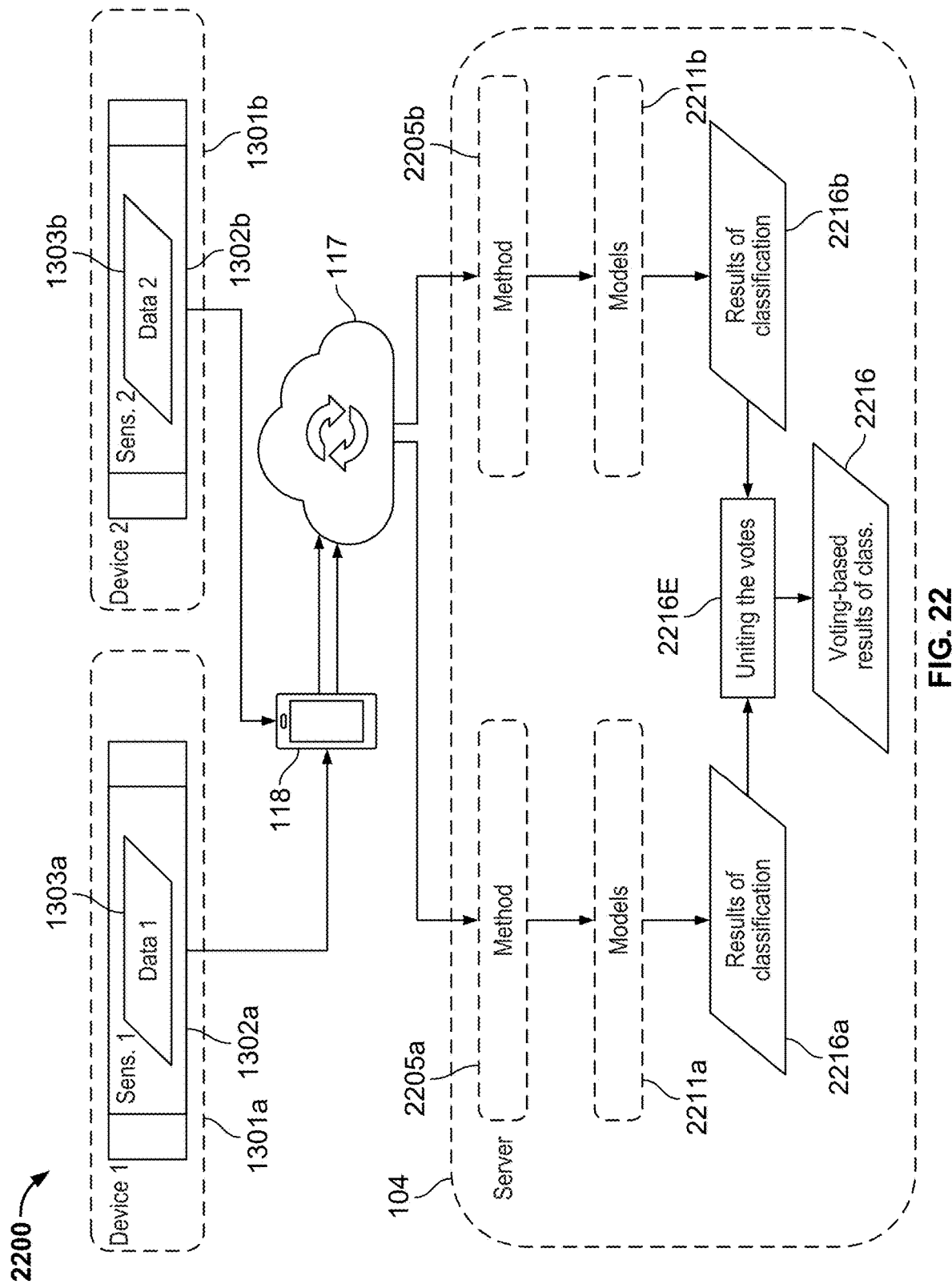
FIG. 22 shows an implementation of a two-device fall detection system when the computational method processes the data separately, as independent entities.

FIG. 22 shows an implementation of a two-device fall detection system when the computational method processes the data separately, as independent entities. This results in independent machine learning models that get trained each on its own dataset and thus rendering their classifications independently from one another, so that the final decision about every observation is taken by evaluating the models' votes in conjunction.

An example of the separate consideration of the data from multiple motion sensors is shown in FIG. 22 that illustrates a system 2200 comprising the same two wearable devices 1301*a* and 1301*b* with two motion sensors 1302*a* and 1302*b* that record two one-sensor data 1303*a* and 1303*b*, respectively, as shown in FIG. 13.

However, unlike the system 1300 that considers the two-sensor data 1303*a,b* jointly, the system 2200 processes them independently using two computational methods 2205*a,b* and two independent groups of method-specific machine learning models 2211*a,b*.

In the training mode, after the models are independently taught on training datasets, for every observation from the testing dataset within the data 1303*a,b* each of the models gets validated, so that the subsequent minimization over the fall-related total false rates ultimately produces optimal method-specific machine learning models with their own results of classification 2216*a* and 2216*b* (called "votes"), respectively.

An additional computational method 2216E (the "elector") evaluates the votes made by the optimal method-specific machine learning models, thus defining the ultimate, voting-based machine learning model (the "optimal V-model") and producing the ultimate classifications 2216.

In the execution mode the computational methods take a new portion of the stream data, process it independently, extract anomalies, calculate their properties, and forward the outputs to the optimal method-specific machine learning models for classification. The elector evaluates the votes of the optimal method-specific machine learning models, providing the ultimate, voting-based classification.

In practice the number of the independent computational methods, and hence, the number of the votes made by the optimal method-specific machine learning models that constitute the optimal V-model can be odd to avoid uncertainty that appears when half of the votes is made for a fall, while the other half is made for a daily activity.

In some implementations a multiple-device voting-based system can exploit a mixture of a joint and a separate processing of the data recorded by the multiple sensors. For example, in the case of p≥2 wearables devices, such a system can implement a joint processing of the p-sensor data using a wavelet-based total coherence method and simultaneously implement a separate processing of the p independent one-sensor time series using p methods based on continuous wavelet transform. Then for every observation there appears p+1 votes, one made by the C-model and the p other votes made by the p T-models.

Figure 23:
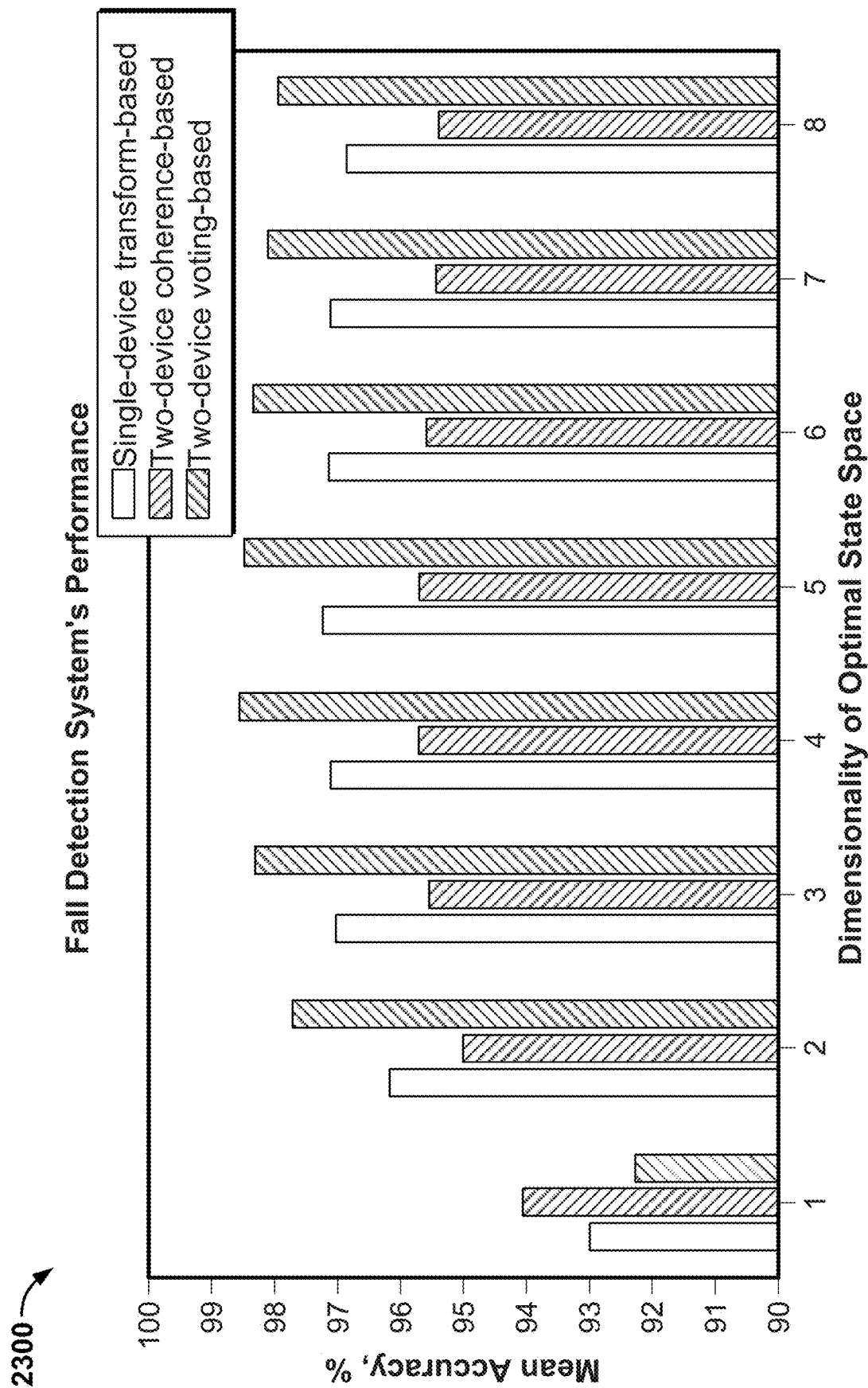
FIG. 23 shows a comparison of the performance of a single-device transform-based system, a two-device coherence-based system, and a two-device voting-based system in terms of the mean classification accuracy.
Figure 24:
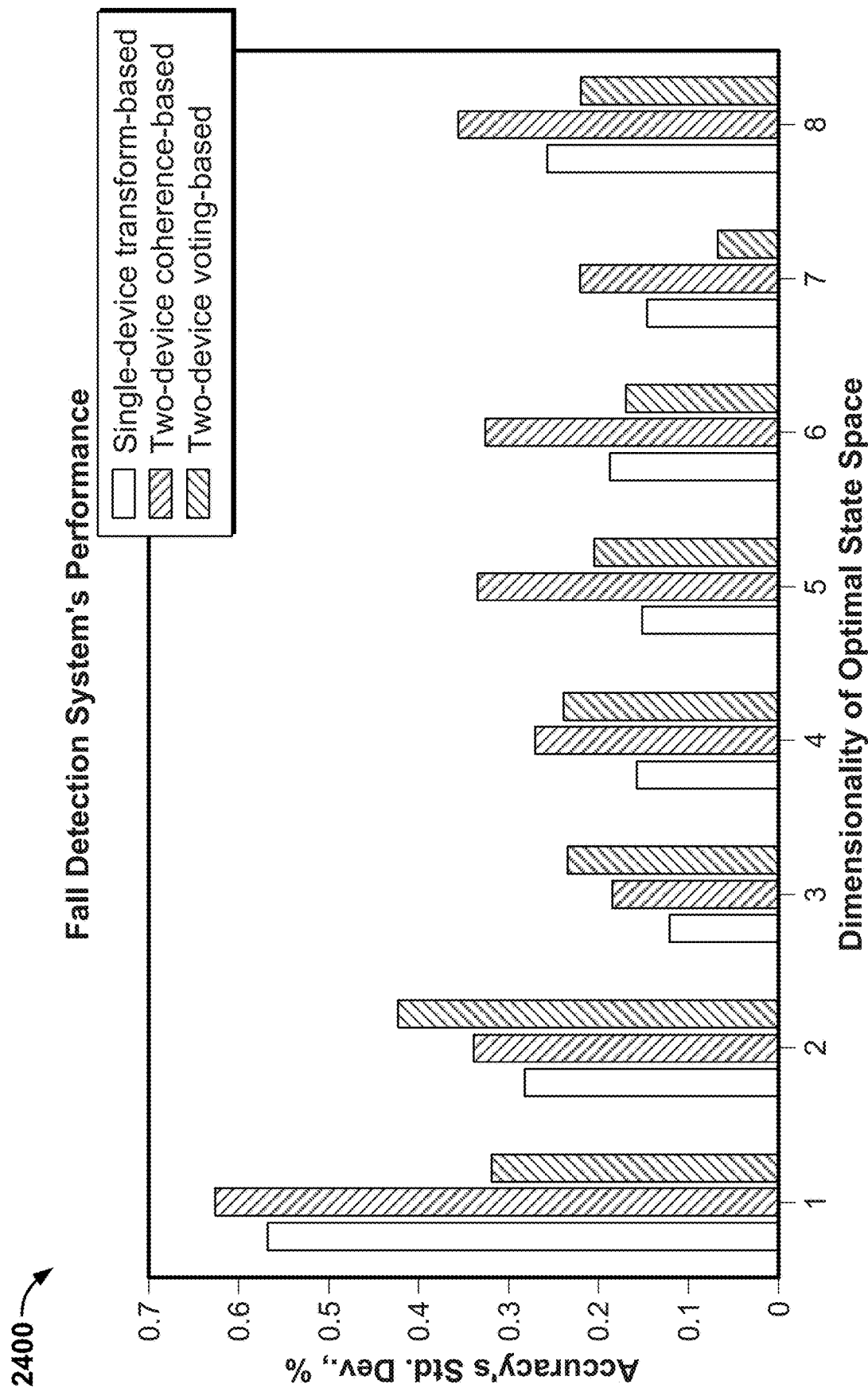
FIG. 24 shows a comparison of the performance of a single-device transform-based system, a two-device coherence-based system and a two-device voting-based system in terms of the standard deviation from the mean classification accuracy.

A comparison of the performance of a single-device transform-based system, a two-device coherence-based system, and a two-device voting-based system is shown in FIG. 23 (a bar chart 2300 for the mean classification accuracy) and FIG. 24 (a bar chart 2400 for the standard deviation). The two-device voting-based system exploits a mixture of the joint, coherence-based processing of the data considered as a single two-sensor entity, and of the two separate, transform-based processings of the same data considered as two independent single-sensor time series. Each of the observation data is a 15-seconds-long time series containing either a fall or a non-fall-related activity. The entire dataset contains 776 randomly chosen portions of the data recorded during 8-hours-long daily life by ten healthy male and female volunteers aged 22 to 45 years.

As it is seen from FIG. 23, the two-device voting-based system demonstrates a more accurate classification in almost all optimal state spaces, with the maximum of 98.5% in the four-dimensional space. At the same time, FIG. 24 evinces the classification accuracy's standard deviation for this system does not exceed 0.25% in the spaces of dimensionality 3 to 8. These results demonstrate the benefits of using multiple-device systems for accurate fall detection. Besides, given the ability of coherence-based methods to predict the appearance of critical events in advance, this indicates a potential of using multiple-device systems, exploiting coherence as their integral part, in the perspective of tackling the yet unsolved problem of fall prediction.

The making of fall detection systems using data from multiple wearable devices is not limited by the above-described implementations. Elements of one or more implementations can be added, eliminated, or combined to produce further implementations. Computational methods based on other mathematical tools, distinct from two-dimensional time-frequency transforms and/or wavelet-based coherence fields, as well as machine/deep learning models based on statistical methods distinct from support vector machines, e.g., decision trees, logistic regressions, naïve Bayes classifiers, and others, can be used. Moreover, data of other types, distinct from multidimensional acceleration vectors, e.g., magnetic field around the device, can be involved. Given that, all such implementations are within the scope of the claims stated below.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method comprising:
    receiving, at a wearable device worn by a user, motion data based on the user's activities over a period of time, wherein the wearable device includes a motion sensor, wherein the motion sensor includes a first motion sensor worn on a first wrist of the user, and a second motion sensor worn on a second wrist of the user, wherein the motion sensor collects acceleration data, the acceleration data including data indicating a first wrist acceleration and a second wrist acceleration, wherein the acceleration data relates to the motion data, wherein the wearable device communicates with a server;

calculating one or more properties of the motion data, comprising:
calculating a two-dimensional data transform of the motion data;
determining, using the two-dimensional data transform, an area where the transform's values exceed a threshold; and
calculating one or more properties of the area;

determining that the user fell using a machine learning model executed on a processor of a cloud service and based on the one or more properties of the motion data, wherein the machine learning model was previously trained on historical motion data; and transmitting the determination to the server, a caretaker of the user, and an emergency system.

2. The method of claim 1, wherein the machine learning model was previously trained either on a person-specific basis, using historical motion data associated with the user's past activities, or on a universal basis, using historical motion data associated with past activities of a cohort of users, wherein the historical motion data was recorded using the motion sensor of the wearable device.

3. The method of claim 1, wherein the motion data recorded by the motion sensor is a one-or more component vector measuring the user's acceleration over the period of time at a rate of at least 20 Hz.

4. The method of claim 1, wherein the two-dimensional data transform is indicative of time-frequency features of the motion data.

5. The method of claim 1, wherein the one or more properties of the area are indicative of time-frequency features of the area.

6. The method of claim 1, wherein the using the machine learning model executed on the processor further comprises evaluating a state of the user's current activity.

7. The method of claim 6, wherein the evaluation of the user's current activity is performed by classifying one or more properties of an area against a previously determined optimal state space based on an analysis of the historical data.

8. A computer program product embodied in a non-transitory computer readable medium and comprising computer instructions for:

receiving, at a wearable device worn by a user, motion data based on the user's activities over a period of time, wherein the wearable device includes a motion sensor, wherein the motion sensor includes a first motion sensor worn on a first wrist of the user, and a second motion sensor worn on a second wrist of the user, wherein the motion sensor collects acceleration data, the acceleration data including data indicating a first wrist acceleration and a second wrist acceleration, wherein the acceleration data relates to the motion data, wherein the wearable device communicate with a server;

calculating one or more properties of the motion data, comprising:
calculating a two-dimensional data transform of the motion data;
determining, using the two-dimensional data transform, an area where the transform's values exceed a threshold; and
calculating one or more properties of the area;

determining that the user fell using a machine learning model executed on a processor of a cloud service and based on the one or more properties of the motion data, wherein the machine learning model was previously trained on historical motion data; and transmitting the determination to the server, a caretaker of the user, and an emergency system.

9. The computer program product of claim 8, wherein the machine learning model was previously trained either on a person-specific basis, using historical motion data associated with the user's past activities, or on a universal basis, using historical motion data associated with past activities of a cohort of users, wherein the historical motion data was recorded using the motion sensors of the wearable device.

10. The computer program product of claim 8, wherein the motion data recorded by the motion sensor is a one- or more component vector measuring the user's acceleration over the period of time at a rate of at least 20 Hz.

11. The computer program product of claim 8, wherein the two-dimensional data transform is indicative of time-frequency features of the motion data.

12. The computer program product of claim 8, wherein the one or more properties of the area are indicative of time-frequency features of the area.

13. The computer program product of claim 8, wherein using the machine learning model executed on the processor further comprises evaluating a state of the user's current activity.

14. The computer program product of claim 13, wherein the evaluation of the user's current activity is computed by classifying one or more properties of an area against a previously determined optimal state space based on an analysis of the historical motion data.

15. A system comprising:
a processor configured to:
receive, at a wearable device worn by a user, motion data based on the user's activities over a period of time, wherein the wearable device includes a motion sensor, wherein the motion sensor includes a first motion sensor worn on a first wrist of the user, and a second motion sensor worn on a second wrist of the user, wherein the motion sensor collects acceleration data, the acceleration data including data indicating a first wrist acceleration and a second wrist acceleration, wherein the acceleration data relates to the motion data, wherein the wearable device communicates with a server;
calculate one or more properties of the motion data, comprising to:
calculate a two-dimensional data transform of the motion data;
determine, using the two-dimensional data transform, an area where the transform's values exceed a threshold; and
calculate one or more properties of the area;
determine that the user fell using a machine learning model executed on a processor of a cloud service and based on the one or more properties of the motion data, wherein the machine learning model was previously trained on historical motion data; and
transmit the determination to the server, a caretaker of the user, and an emergency system; and
a memory coupled to the processor and configured to provide the processor with instructions.

16. The system of claim 15, wherein the machine learning model was previously trained either on a person-specific basis, using historical motion data associated with the user's past activities, or on a universal basis, using historical motion data associated with past activities of a cohort of users, wherein the historical motion data was recorded using the motion sensor of the wearable device.

17. The system of claim 15, wherein the motion data recorded by the motion sensor is a one-or more component vector measuring acceleration over the period of time at a rate of at least 20 Hz.

18. The system of claim 15, wherein the two-dimensional data transform is indicative of time-frequency features of the motion data.

19. The system of claim 15, wherein the using the machine learning model executed on the processor further comprises evaluating of a state of the user's current activity.

20. The system of claim 19, wherein the evaluation of the user's current activity is performed by classifying one or more properties of an area against a previously determined optimal state space based on an analysis of the historical motion data.

* * * * *